US011129801B2

(12) United States Patent
Roman et al.

(10) Patent No.: US 11,129,801 B2
(45) Date of Patent: Sep. 28, 2021

(54) IGMESINE FOR USE IN THE TREATMENT OF NEURODEGENERATIVE DISEASES

(71) Applicant: SigmaThera SAS, Montferrier-sur-Lez (FR)

(72) Inventors: François J. Roman, Clermont l'Herault (FR); Johann Meunier, Mauguio (FR)

(73) Assignee: SigmaThera SAS, Montferrier-sur-Lez (FR)

( * ) Notice: Subject to any disclaimer, the term of this patent is extended or adjusted under 35 U.S.C. 154(b) by 123 days.

(21) Appl. No.: 16/076,504

(22) PCT Filed: Feb. 10, 2017

(86) PCT No.: PCT/EP2017/053066
§ 371 (c)(1),
(2) Date: Aug. 8, 2018

(87) PCT Pub. No.: WO2017/137600
PCT Pub. Date: Aug. 17, 2017

(65) Prior Publication Data
US 2019/0046472 A1    Feb. 14, 2019

Related U.S. Application Data

(60) Provisional application No. 62/293,832, filed on Feb. 11, 2016.

(51) Int. Cl.
| | | |
|---|---|---|
| *A61K 31/137* | (2006.01) | |
| *A61K 9/00* | (2006.01) | |
| *A61P 25/16* | (2006.01) | |
| *A61P 25/28* | (2006.01) | |
| *A61K 31/192* | (2006.01) | |
| *A61K 31/40* | (2006.01) | |
| *A61K 31/445* | (2006.01) | |
| *A61K 45/06* | (2006.01) | |

(52) U.S. Cl.
CPC .......... *A61K 31/137* (2013.01); *A61K 9/0053* (2013.01); *A61K 31/192* (2013.01); *A61K 31/40* (2013.01); *A61K 31/445* (2013.01); *A61K 45/06* (2013.01); *A61P 25/16* (2018.01); *A61P 25/28* (2018.01); *A61K 2300/00* (2013.01)

(58) Field of Classification Search
CPC .... A61K 31/137; A61K 45/06; A61K 31/445; A61K 31/40; A61K 31/192; A61K 9/0053; A61K 2300/00; A61P 25/16; A61P 25/28
See application file for complete search history.

(56) References Cited

U.S. PATENT DOCUMENTS

| | | | |
|---|---|---|---|
| 5,034,419 A | * | 7/1991 | Aubard ................ C07C 211/28 514/438 |
| 6,436,938 B1 | | 8/2002 | Howard, Jr. |
| 2003/0013699 A1 | * | 1/2003 | Davis ................... A61K 31/366 514/210.02 |
| 2005/0020483 A1 | | 1/2005 | Oksenberg et al. |
| 2007/0123556 A1 | | 5/2007 | Pennypacker et al. |

FOREIGN PATENT DOCUMENTS

| | | |
|---|---|---|
| EP | 0115685 A1 | 3/2001 |
| WO | WO-00/41684 | 7/2000 |
| WO | 2001015685 A1 | 3/2001 |
| WO | WO-2004-110387 A2 | 12/2004 |
| WO | WO-2016-138135 A1 | 9/2016 |
| WO | 2017137600 A1 | 8/2017 |

OTHER PUBLICATIONS

Urani et al. Enhanced antidepressant efficacy of σ1 receptor agonists in rats after chronic intracerebroventricular infusion of β-amyloid-(1-40) protein, European Journal of Pharmacology 486 (2004) 151-161 (Year: 2004).*
Dosage guide for ibuprofen (Year: 2019).*
Dosage guide for selegiline (Year: 2019).*
Dosage guide for donepezil (Year: 2019).*
International Search Report dated Apr. 12, 2017 for International Application No. PCT/EP2017/053066, filed Feb. 10, 2017.
Michael O'Neill et al., "The [sigma] receptor ligand JO 1784 (igmesine hydrochloride) is neuroprotective in the gerbil model of global cerebral ischaemia", European Journal of Pharmacology, vol. 283, No. 1-3, Sep. 1, 1995, pp. 217-225.
Johann Meunier et al., "Antiamnesic and neuroprotective effects of donepezil against learning impairments induced in mice by exposure to carbon monoxide gas", Journal of Pharmacology and Experimental Therapeutics, American Society for Pharmacology and Experimental Therapeutics, US, vol. 317, No. 3, Jun. 1, 2006, pp. 1307-1319.
Chavant, F. et al., (2010). "Imipramine, in part through tumor necrosis factor alpha inhibition, prevents cognitive decline in beta-amyloid accumulation in a mouse model of Alzheimer's disease." The Journal of Pharmacology and Experimental Therapeutics 332(2):505-514.
Donepezil Dosage Guide (last updated Feb. 14, 2019). 2 pages.
Heneka, M. et al., (2015). "Neuroinflammation in Alzheimer's disease." Lancet Neurobiology 14:388-405.
Ibuprofen Dosage Guide (last updated Aug. 14, 2019). 9 pages.
Klementiev, B. et al., (2007). "A neural cell adhesion molecule-derived peptide reduces neuropathological signs and cognitive impairment induced by ABeta25-35." Neuroscience 145:209-224.
Maurice, T. et al., (2009). "The pharmacology of Sigma-1 receptors." Pharmacology & Therapeutics 124(2):195-206.
Meunier, J. et al., (2015). "Brain toxicity and inflammation induced in vivo in mice by the amyloid-beta forty-two inducer aftin-4, a roscovitine derivative." Journal of Alzheimer's Disease 44:507-524.

(Continued)

*Primary Examiner* — Sarah Pihonak
*Assistant Examiner* — Jason Deck
(74) *Attorney, Agent, or Firm* — Muriel Liberto, Esq.; Mintz Levin Cohn Ferris Glovsky and Popeo, P.C.

(57) ABSTRACT

The present invention relates to methods for treating neurodegenerative diseases and disorders with igmesine.

25 Claims, 21 Drawing Sheets

(56) References Cited

OTHER PUBLICATIONS

Selegiline Dosage Guide (last updated Jan. 10, 2018). 4 pages.

Urani, A. et al., (2004). "Enhanced antidpressant efficacy of theta1 receptor agonists in rats after chronic intracerebroventricular infusion of beta-amyloid-(1-40) protein." European Journal of Pharmaceology 486:151-161.

Akunne, H.C. et al. (2001). "Neuropharmacological profile of a selective sigma ligand, igmesine: a potential antidepressant." Neuropharmacology 41(2001):138-149.

Kinsora, J.J. Jr. et al. (1998). "Effects of igmesine in preclinical antidepressant tests." Society for Neuroscience Abstract 291.3, in Neuropsychiatric Disorders IV, vol. 24 (1998), p. 744. 1 page.

Leadbetter, R. et al. (1999). "Igmesine: A novel antidepressant." Biological Psychiatry, 1999; 45:1S-147S, Abstract 244, p. 76S (Friday Abstracts). 1 page.

Maurice, T. et al. (1996). "Beneficial effects of sigma agonists on the age-related learning impairment in the senescence-accelerated mouse (SAM)." Brain Research 733(1996):219-230.

Maurice, T. (2016). "Protection by sigma-1 receptor agonists is synergic with donepezil, but not with memantine, in a mouse model of amyloid-induced memory impairments." Behavioural Brain Research. 296(2016):270-278.

Pande, A.C. et al. (2016). "Igmesine, a novel sigma ligand, has antidepressant properties." In: Genetics of Personality Traits and Disorders (Genetics Symposium, Part 1), Abstract SM0505, pS8. 1 page.

Roman, F. J. et al. (1990). JO 1784, a potent and selective ligand for rat and mouse brain sigma-sites. Journal of Pharmacy and Pharmacology 42:439-440.

Villard, V. et al. (2011). "Pharmacological interaction with the Sigma1 (sigma1)-receptor in the acute behavioral of effects antidepressants." Journal of Pharmacological Science 115:279-292.

Volz, H.P. et al. (2004). "Clinical trials with sigma ligands." Pharmacopsychiatry 37 Supplement 3: S214-S220. 7 pages.

Pande, A.C. et al. (1998). "Igmesine, a novel sigma ligand, has antidepressant properties." Presented at Genetics Symposium: Genetics of Personality Traits and Disorders. Abstract SM0505, pS8. 1 page.

Pande A.C. et al. (1999). "A placebo-controlled trial of igmesine in the treatment of major depression." In New Mechanisms and Strategies for Treating Depression. Abstract S.03.01. 1 page.

* cited by examiner

IGMESINE FOR USE IN THE TREATMENT OF NEURODEGENERATIVE DISEASES

RELATED APPLICATION

This application is a national stage entry, filed under 35 U.S.C. § 371, of International Application No. PCT/EP2017/053066, filed on Feb. 10, 2017, which claims priority from U.S. Provisional Patent Application Ser. No. 62/293,832, filed Feb. 11, 2016, the contents of which are hereby fully incorporated by reference.

FIELD OF THE INVENTION

The present invention relates to methods for treating neurodegenerative diseases and disorders with compositions comprising igmesine.

BACKGROUND OF THE INVENTION

Sigma receptors are non-opioid, non-phencyclidine (PCP) binding sites which modulate cell survival and excitability. Sigma receptors are membrane associated proteins widely distributed in the mammalian brain, peripheral neurons, and visceral organs. Two subtypes, sigma-1 and sigma-2, have been identified based on their pharmacological profiles (Seth P et al. (1998) *J Neurochem.* 70:922-931). Both sigma receptor subtypes are widely distributed in the central nervous system (CNS). The sigma-1 receptor (sigma-1R) is a chaperon protein localized in the endoplasmic reticulum (ER) and at the ER-mitochondria interface in brain tissues, where it regulates ER-mitochondrion Ca(2+) signaling and ER-nucleus crosstalk through the prostacycline (IP) receptor (Hayashi T et al., 2007 *Cell* 131:596-610). In humans, sigma-1R is encoded by the SIGMA1R gene. The sigma-2 receptor (sigma-2R) is found in several areas of the brain, including in the cerebellum, motor cortex, and substantia nigra. Its position has not yet been located on the human chromosome.

A number of studies have indicated that sigma-1R has neuroprotective activity. For example, in vitro studies have shown protective effects for sigma-1R agonists in a variety of cells, including primary cerebral neurons, retinal ganglion cells, and lens cells. In addition, knockdown of sigma-1R increases the vulnerability of cells to highly toxic amyloid $A\beta_{25-35}$ peptide, oxidative stress, ER stress, and glucose deprivation (Hall A A et al. (2009) *Glia* 57(7): 744-754; Schroder M et al. (2005). *Mutation Res.* 569(1-2): 29-63). Sigma-1R agonists have also shown efficacy against oxidative stress and vulnerability to $A\beta_{25-35}$ peptide in animal models. The potent sigma-1 ligand, 4-phenyl-1-(4-phenylbutyl) piperidine (PPBP), attenuated infarction volume in cerebral cortex and striatum induced by occlusion/reperfusion of the middle cerebral artery in experimental animals and markedly attenuated nitric oxide (NO) producton in schemic and nonischemic stiratum (Goyagi et al. (2001) *Stroke* 32(7): 1613-1620). In addition, a selective sigma-1R agonist, PRE-084, attenuated $A\beta_{25-35}$ peptide-induced lipid peroxidation in the murine hippocampus (Meunier J et al. (2006). *Br J Pharmacol* 149(8): 998-1012).

Accumulating evidence suggests that Sigma-1R plays a role in both the pathophysiology of neuropsychiatric diseases, and the mechanistic action of some therapeutic drugs (Nitsu T et al. (2012) *Curr Phar Des.* 18:875-83). Sigma-1R as a target for therapeutic intervention has been suggested in various conditions based upon its purported neuroprotective and/or anti-inflammatory activities. For example, sigma receptor ligands have been suggested for the treatment of the movement disorders elicited by methamphetamine (Matsumoto R R et al. (2008) *Eur. Neuropsychopharmacology* 18(12): 871-881). Sigma receptor agonists including fluvoxamine, N-(N-Benzylpiperidin-4-yl)-4-iodobenzamide (4-IBP), PRE-084, [N-(1,4-diphenyl-1-ethyl-3-buten-1-yl)-N-methyl-cyclopropanemethanamine hydrochloride (igmesine), OPC-14523, BD-737, and N-benzyl-N'-(2-hydroxy-3,4-dimethoxybenzyl)-piperazine (BHDP) have also been proposed for treating or preventing neurodegenerative disease caused by ischemic stroke, Alzheimer's disease, diabetic peripheral neuropathy, cancer therapy induced neuropathy, multiple sclerosis, amyotrophic lateral sclerosis, traumatic brain injury, spinal cord injury, Huntington's disease, or Parkinson's disease (US2005/0020483). US 2005/0070524 describes compositions of a cyclooxygenase-2 selective inhibitor and an anticonvulsant agent for the treatment of central nervous system disorders, and igmesine is listed among the possible anticonvulsant agents. U.S. Pat. No. 5,665,725 describes certain piperidine derivatives that are sigma receptor ligands and which are said to be useful in the treatment of anxiety, psychosis, epilepsy, convulsion, movement disorders, motor disturbances, amnesia, cerebrovascular diseases, senile dementia of the Alzheimer type and Parkinson's disease. US 2007/0123556 describes methods of post-stroke treatment at delayed time points with sigma receptor agonists including 1,3-di-o-tolyguanidine (DTG), carbetapentane, (+)-pentazocine, PRE-084, rimcazole, L-687,384, BD-737, and igmesine. A recent paper reports memory enhancement by the sigma-1 receptor agonists PRE-84 and ANAVEX2-73 in a mouse model of β-amyloid-induced memory impairments, and synergistic activity with donepezil when the compounds are administered in a preventive and symptomatic manner (Maurice T (2016) *Behavioural Brain Res.* 296: 270-278). However, no data showing the effect of the sigma-1R agonists on neuroprotection associated with the memory enhancement is provided.

Igmesine (JO-1784) is a potent and highly selective sigma-1R agonist with $IC_{50}$ of 39±8 nM, (Roman F J et al. (1990) *J. Pharm. Pharmacology* 42(6): 439-440). This affinity is similar to that of haloperidol (24±6 nM) which is one of the most active compounds for this site (Largent B L, et al. (1986) *J. Pharmacology Exp. Therap.* 238(2): 739-748). JO-1783, the inactive stereoisomer of igmesine (JO-1784), was ten times less potent than igmesine, indicating a certain degree of stereospecificity of the compound for the binding site.

Igmesine has neuroprotective effects in the gerbil model of global cerebral ischemia at effective doses of 50, 75, and 100 mg/kg. (O'Neill M et al. (1995) *Eur. J. Pharmacol.* 283(1-3): 217-225) and has also shown beneficial effects on the age-related memory impairment in the senescence-accelerated mouse model at effective doses of from 0.1 to 3 mg/kg in an acute treatment paradigm. (Maurice T et al. (1996) *Brain Research* 733(2): 219-230. U.S. Pat. No. 5,034,419) (L'Oreal) describes igmesine and related compounds and, on the basis of the affinity found in vitro for sigma receptors, proposes its use in therapy for neurological and/or mental disorders generally, including by way of example depressive states, memory and/or behavioral disturbances, schizophrenia, Alzheimer's disease, Parkinson's disease and senile dementia. However, no data are provided to support therapeutic efficacy in any of these conditions.

The antidepressant efficacy of igmesine was suggested in some pre-clinical animal models (Kinsora J J Jr et al. (1998) *Neurosci. Abstr.* 24, 291.3; Matsuno K et al. (1996) *Eur. J.*

Pharmacol. 312(3): 267-271; Song C et al. (1997). *Neuropsychobiology* 35(4): 200-204; Urani A et al. (2001) *J. Pharmacol. Exp. Therap.* 298(3): 1269-1279) and antidepressant activity was also observed in the clinical trials (Pande A C et al. (1998). *Int. J. Neuropsychopharmacol.* 1: S8-S9; Pande A C et al. (1999) *Eur. Neuropsychopharmacol.* 9: S138; Leadbetter R, et al. (1999) *Biol. Psychiatry,* 45 (Suppl) p. 76S (Abs. Z44)). A number of patent applications describe the methods for treating depression using igmesine. For example, WO 2000/041684 describes methods for treating depression by administering a combination of a sigma-1R agonist, e.g., igmesine, and a serotonin re-uptake inhibitor, e.g., fluoxetine. WO 2001/015685 describes a beneficial effect on the anti-depressant activity of igmesine when administered to steroid-depleted animals. Igmesine has also been described as useful in treating depression when administered in combination with a serotonin re-uptake inhibitor, for example in U.S. Pat. No. 6,436,938 (Pfizer).

US 2003/0013699 (Schering Corp.) describes methods of treating Alzheimer's disease using certain compounds defined by their chemical formulas and their use in combination therapy, reciting sigma receptor ligands among the many possible agents that might theoretically be used in such combination therapy.

To date, no data are published describing the therapeutic effect of igmesine in Alzheimer's disease, amyoptrophic lateral sclerosis, multiple sclerosis, Parkinson's disease, Huntington's disease or frontotemporal degeneration.

SUMMARY OF THE INVENTION

The present invention is based, in part, on the surprising finding that igmesine has potent neuroprotective effects in the $A\beta_{25-35}$ mouse model of Alzheimer's disease, as evidenced by its ability to prevent or substantially reduce $A\beta_{25-35}$ induced neurotoxicity in this model system, as evidenced, for example, by the prevention of the learning and memory deficits characteristic of $A\beta_{25-35}$ induced neurotoxicity, as well as by cellular and biochemical indicators, such as reducing neuronal cell apoptosis, reducing endoplasmic reticulum (ER) stress, reducing neuroinflammation, reducing beta-amyloid burden, and inhibiting tau protein hyperphosphorylation. The present invention is also based, in part, on the finding that igmesine is able to prevent the appearance of learning and memory deficits elicited by $A\beta_{25-35}$ induced neurotoxicity and which are associated with both spatial working memory and contextual long-term memory. The effective dose range for igmesine was in the order of 10 to 100-fold lower than the effective dose range previously observed in humans, for example, in connection with its anti-depressant effects, and in rodents, for example, in connection with its neuroprotective effects in models of global cerebral ischemia. In addition, the present invention is based, in part, on the finding that igmesine acts synergistically with other therapeutic agents to prevent or substantially reduce $A\beta_{25-35}$ induced neurotoxicity. The present invention is also based, in part, on the ability of igmesine to reduce or prevent neuronal cell apoptosis. The present invention is also based, in part, on the ability of igmesine to promote the chaperone activity of sigma-1 receptors to attenuate the accumulation of misfolded proteins that underlie neurodegenerative pathologies like Alzheimer's disease, amyotrophic lateral sclerosis (ALS), Huntington's disease, multiple sclerosis, Parkinson's disease and frontotemporal degeneration.

Accordingly, the present disclosure provides compositions and methods for treating a neurodegenerative disease or disorder using igmesine, either alone, or in combination with one or more additional therapeutic agents. In embodiments, the one or more additional therapeutic agents is selected from a cholinesterase inhibitor, an $A\beta$ toxicity lowering agent, a hormone replacement agent, a lipid-lowering agent, a secretase modulating agent, an $A\beta$ aggregation inhibitor, a neurofibrillary inhibitor, a monoamine oxidase (MAO) inhibitor, and a $\beta$-amyloid catabolism inhibitor. In embodiments, the one or more additional therapeutic agents is a cholinesterase inhibitor. In embodiments, the cholinesterase inhibitor is donepezil. In embodiments, the one or more additional therapeutic agents is an anti-inflammatory agent. In embodiments, the anti-inflammatory agent is a non-steroidal anti-inflammatory agent. In one embodiment, the anti-inflammatory agent is ibuprofen. In embodiments, the one or more additional therapeutic agents is a lipid-lowering agent. In embodiments, the lipid-lowering agent is a statin. In embodiments, the statin is simvastatin or atorvastatin. In embodiments, the one or more additional therapeutic agents is a MAO inhibitor. In embodiments, the MAO inhibitor is selected from rasagiline, selegiline and tranylcypromine. In embodiments, the MAO inhibitor is a MAO-B inhibitor. In embodiments, the MAO-B inhibitor is selegiline.

In one embodiment, the present disclosure provides a composition for use in treating a neurological disease or disorder in a human subject in need thereof, the composition being adapted for once or twice daily dosing and comprising an amount of igmesine, or a pharmaceutically acceptable salt thereof, effective to ameliorate or delay the onset of one or more pathophysiological characteristics of the disease or disorder, or ameliorate or delay the onset of at least one clinical symptom of the disease or disorder, wherein the amount of igmesine in the composition is in the range of from 1 to 20 mg or from 1 to 15 mg, preferably from 1 to 10 mg or from 1 to 5 mg.

In one embodiment, the disclosure provides a method for treating a neurological disease or disorder in a human subject in need thereof, the method comprising administering to the subject a pharmaceutical composition comprising a therapeutically effective amount of igmesine, or a pharmaceutically acceptable salt thereof, the amount of igmesine being effective to ameliorate or delay the onset of one or more pathophysiological characteristics of the disease or disorder, or ameliorate or delay the onset of at least one clinical symptom of the disease or disorder, and the amount of igmesine being in the range of from 1 to 20 mg, preferably from 1 to 10 mg.

In embodiments, the neurological disease or disorder is selected from Alzheimer's disease, ALS, Huntington's disease, multiple sclerosis, Parkinson's disease and frontotemporal degeneration.

In one embodiment, the disclosure provides a composition for use in treating Alzheimer's disease in a human subject, the composition comprising igmesine hydrochloride in an amount of from 1 to 100 mg, from 1 to 20 mg, from 1 to 10 mg, from 1 to 5 mg, or from 1 to 3 mg, and one or more additional therapeutic agents. In embodiments, the one or more additional therapeutic agents is selected from a cholinesterase inhibitor, an anti-inflammatory agent, a lipid-lowering agent, and a MAO inhibitor. In embodiments, the cholinesterase inhibitor is donepezil. In embodiments, the amount of the donepezil in the composition is from 1 to 6 mg. In embodiments, the anti-inflammatory agent is a non-steroidal anti-inflammatory agent. In one embodiment, the anti-inflammatory agent is ibuprofen. In embodiments, the one or more additional therapeutic agents is a lipid-lowering agent. In embodiments, the lipid-lowering agent is a statin. In embodiments, the statin is simvastatin or atorvastatin. In embodiments, the one or more additional therapeutic agents is a MAO inhibitor. In embodiments, the MAO inhibitor is selected from rasagiline, selegiline and tranylcypromine. In embodiments, the MAO inhibitor is a MAO-B inhibitor. In embodiments, the MAO-B inhibitor is selegiline.

In one embodiment, the disclosure provides a method of treating Alzheimer's disease in a human subject in need thereof, the method comprising administering to the subject a pharmaceutical composition comprising a therapeutically effective amount of igmesine, or a pharmaceutically acceptable salt thereof, the amount of igmesine being effective to ameliorate or delay the onset of one or more pathophysiological characteristics of Alzheimer's disease, or ameliorate or delay the onset of at least one clinical symptom of Alzheimer's disease, the amount of igmesine being in the range of from 1 to 100 mg, from 1 to 50 mg, from 1 to 20 mg, from 1 to 10 mg, or from 1 to 5 mg. In embodiments, the composition further comprises one or more additional therapeutic agents, in addition to the igmesine. In embodiments, the one or more additional therapeutic agents is selected from a cholinesterase inhibitor, an anti-inflammatory agent, a lipid-lowering agent, and a MAO inhibitor. In embodiments, the cholinesterase inhibitor is donepezil. In embodiments, the amount of the donepezil in the composition is from 1 to 6 mg. In embodiments, the anti-inflammatory agent is a non-steroidal anti-inflammatory agent. In one embodiment, the anti-inflammatory agent is ibuprofen. In embodiments, the one or more additional therapeutic agents is a lipid-lowering agent. In embodiments, the lipid-lowering agent is a statin. In embodiments, the statin is simvastatin or atorvastatin. In embodiments, the one or more additional therapeutic agents is a MAO inhibitor. In embodiments, the MAO inhibitor is selected from rasagiline, selegiline and tranylcypromine. In embodiments, the MAO inhibitor is a MAO-B inhibitor. In embodiments, the MAO-B inhibitor is selegiline.

In accordance with any of the embodiments of methods or compositions described herein, the pharmaceutically acceptable salt of igmesine may be the hydrochloride salt.

In embodiments, the subject in need thereof is a human patient diagnosed with the neurological disease or disorder.

In embodiments, the neurological disease or disorder is selected from Alzheimer's disease, amyotrophic lateral sclerosis (ALS), multiple sclerosis, Parkinson's disease, Huntington's disease and frontotemporal degeneration.

In one embodiment, the neurological disease or disorder is Alzheimer's disease. In embodiments, the one or more pathophysiological characteristics of Alzheimer's disease is selected from neuroinflammation, apoptosis, ER stress, β amyloid plaque burden, hyperphosphorylation of tau protein, and lipid peroxidation. In embodiments, the at least one clinical symptom of Alzheimer's disease is a learning or memory deficit associated with one or more of working memory, short term memory, and long term memory. In embodiments, the at least one clinical symptom of Alzheimer's disease is positively reinforced memory or spatial and contextual memory, or both.

In embodiments, a pharmaceutical composition comprising igmesine as described herein further comprises an effective amount of at least one additional active pharmaceutical ingredient ("API"), which may also be referred to interchangeably herein as an "active agent" or "therapeutic agent". In embodiments, the at least one additional API is selected from the group consisting of a cholinesterase inhibitor, an Aβ toxicity lowering agent, a hormone replacement agent, a lipid-lowering agent, a secretase modulating agent, an Aβ aggregation inhibitor, a neurofibrillary inhibitor or a β-amyloid catabolism inhibitor, and combinations thereof. In embodiments, the at least one additional API is selected from a cholinesterase inhibitor, an anti-inflammatory agent, a lipid-lowering agent, and a MAO inhibitor. In embodiments, the cholinesterase inhibitor is donepezil. In embodiments, the amount of the donepezil in the composition is from 1 to 6 mg. In embodiments, the anti-inflammatory agent is a steroidal or non-steroidal anti-inflammatory agent. In one embodiment, the anti-inflammatory agent is ibuprofen. In embodiments, the at least one additional API is a lipid-lowering agent. In embodiments, the lipid-lowering agent is a statin. In embodiments, the statin is simvastatin or atorvastatin. In embodiments, the at least one additional API is a MAO inhibitor. In embodiments, the MAO inhibitor is selected from rasagiline, selegiline and tranylcypromine. In embodiments, the MAO inhibitor is a MAO-B inhibitor. In embodiments, the MAO-B inhibitor is selegiline.

In embodiments, the at least one additional API is a cholinesterase inhibitor. In embodiments, the cholinesterase inhibitor is present in an amount that is at least 2-fold, preferably at least 4-fold, less than the therapeutically effective amount of the cholinesterase inhibitor in the absence of igmesine hydrochloride. In embodiments, the cholinesterase inhibitor is donepezil. In embodiments, the effective amount of the donepezil is from 1 to 6 mg.

In embodiments, the composition is an oral dosage form or a dosage form suitable for intravenous administration.

In embodiments, the disclosure provides a unit dosage form adapted for oral delivery comprising igmesine hydrochloride and donepezil. In embodiments, the amount of igmesine hydrochloride in the unit dosage form is from 1 to 100 mg, from 1 to 20 mg, or from 1 to 10 mg, and the amount of donepezil is from 1 to 6 mg.

In embodiments, the disclosure provides a unit dosage form adapted for oral delivery comprising igmesine hydrochloride and ibuprofen. In embodiments, the amount of igmesine hydrochloride in the unit dosage form is from 1 to 100 mg, from 1 to 20 mg, or from 1 to 10 mg, and the amount of ibuprofen is from 100 to 400 mg.

In embodiments, the disclosure provides a unit dosage form adapted for oral delivery comprising igmesine hydrochloride and simvastatin. In embodiments, the amount of igmesine hydrochloride in the unit dosage form is from 1 to 100 mg, from 1 to 20 mg, or from 1 to 10 mg, and the amount of simvastatin is from 20 to 80 mg.

In embodiments, the disclosure provides a unit dosage form adapted for oral delivery comprising igmesine hydrochloride and atorvastatin. In embodiments, the amount of igmesine hydrochloride in the unit dosage form is from 1 to 100 mg, from 1 to 20 mg, or from 1 to 10 mg, and the amount of atorvastatin is from 10 to 80 mg.

In embodiments, the disclosure provides a unit dosage form adapted for oral delivery comprising igmesine hydrochloride and selegiline. In embodiments, the amount of igmesine hydrochloride in the unit dosage form is from 1 to 100 mg, from 1 to 20 mg, or from 1 to 10 mg, and the amount of selegiline is from 1 to 10 mg.

In embodiments, the disclosure provides a composition for use in treating Alzheimer's disease, Parkinson's disease, Amyotrophic Lateral Sclerosis, or Huntington's disease, in a human subject, the composition comprising igmesine hydrochloride in an amount of from 2.5 to 10 mg per dose, wherein the composition is for administration one, two, or three times daily. In embodiments, the composition further comprises donepezil in an amount of from 1 to 15 mg; or ibuprofen in an amount of from 50 to 150 mg; or selegiline in an amount of from 5 to 15 mg; or atorvastatin in an amount of from 1 to 5 mg.

DETAILED DESCRIPTION OF THE INVENTION

Figure 1:
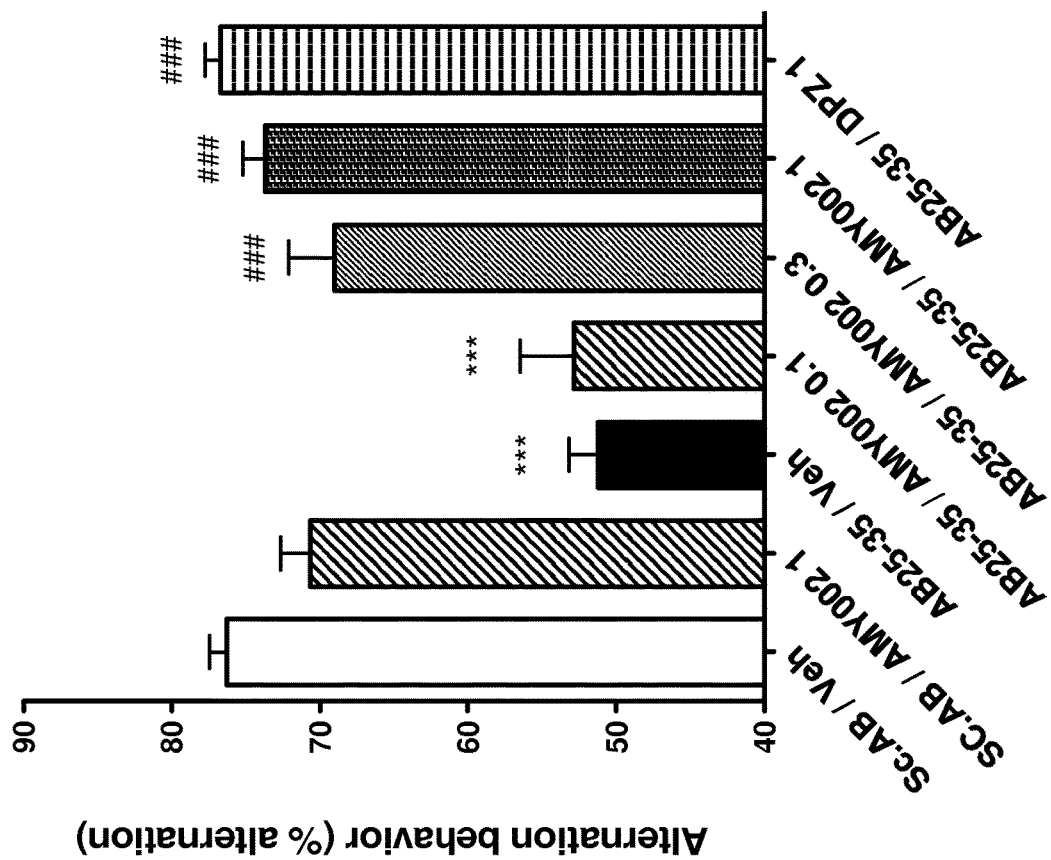
FIG. 1. Effect of the sigma-1R agonist igmesine (AMY002, 0.1, 0.3, 1 mg/kg) on $A\beta_{25-35}$-induced spontaneous alternation in mice. The mice administered Igmesine was i.p. 20 min before intracerebroventricular (i.c.v.) injection of scrambled Aβ peptide (Sc.Aβ) or $A\beta_{25-35}$ (9 nmol) and the mice were tested for the spontaneous alternation behavior using the Y-maze at 7 days post-injection of igmesine. Veh, vehicle solution; DPZ, donepezil (1 mg/kg). *** $p<0.001$ vs. the Veh-plus Sc.Aβ group; ###$p<0.001$ vs. the Veh plus $A\beta_{25-35}$ group; n=12). Data were analyzed by Dunnett's post hoc test. All doses of the treatment in this experiment are expressed in mg/kg.

The present disclosure is based, in part, on the finding that igmesine has a pronounced therapeutic effect at low doses (1 mg/kg) in an acute rodent model of Alzheimer's disease toxicity, the Aβ$_{25-35}$ peptide mouse model. Surprisingly, igmesine prevented the development of various Alzheimer's disease associated pathologies even where treatment was initiated 24 hours after challenge with the Aβ$_{25-35}$ peptide. When igmesine was administered after challenge, its effects were clearly neuroprotective rather than preventive. This result is different from what has been described for other sigma ligands such as PRE-084 and ANAVEX 2-73 evaluated in the same model but using preventive and symptomatic treatment. This particularity is extremely important when considering the translational value of the experimental model. Limitation of efficacy of a therapeutic treatment to a preventive treatment has much limited value considering that patients are in need of medication when they are diagnosed with Alzheimer's disease. Moreover, the only available treatments today are symptomatic treatments such as Aricept™ or Ebixa™ and the limitation of such treatments is largely recognized as being that their benefit cannot be maintained in the long term. All Alzheimer's disease patients eventually outgrow the effects of pharmacotherapy as their condition worsens.

The experimental model used in Example 1 reproduces a possible cause of Alzheimer's disease, which is an excessive production of Aβ oligomers in the brain. Indeed, the Aβ$_{25-35}$ peptide is one of the most toxic that has been found in the brains of dementia patients after autopsy. These results indicate that igmesine can display efficacy even when these toxic peptides have already been injected into the brain in large amounts. Thus, this experiment mimics in an acute protocol the chronic exposure to such toxic peptides in humans during the 15 or 20 years before signs of dementia appear. With these properties, igmesine is fully indicated to be used as a disease modifier, for example, in patients who have been diagnosed in the early stages of Alzheimer's disease, or those at high risk of developing Alzheimer's disease, in order to reduce or even stop the progression of the pathology. In addition, we show here that igmesine synergistically enhanced the therapeutic activity of a cholinesterase inhibitor, donepezil. This synergistic activity was seen with very low doses of igmesine (0.1 mg/kg) combined with a low dose of donepezil, in a range about 4-fold lower than its typical therapeutically effective dose for treating Alzheimer's disease. The low-dose efficacy of igmesine, both alone and in combination with cholinesterase inhibitors, is unexpected based upon prior work with igmesine in both animal models and humans. The possibility of limiting as much as possible exposure to both drugs to get full efficacy is an extremely valuable finding. The synergistic doses are much lower than the doses already known for an acceptable safety in human. As the combination is intended to be used in individuals in need of a treatment for a very long-term treatment from the early diagnosis and all along the rest of their life, the safety of the medication has to be considered as a priority more than in any other indication.

The present disclosure provides that igmesine has potent neuroprotective effects in the Aβ$_{25-35}$ mouse model of Alzheimer's disease, as evidenced by its ability to prevent or substantially reduce Aβ$_{25-35}$ induced neurotoxicity in this model system. Thus, as discussed in more detail infra, igmesine was effective to prevent the learning and memory deficits characteristic of Aβ$_{25-35}$ induced neurotoxicity. Igmesine was also able to reduce or ameliorate several key cellular and biochemical indicators of neurotoxicity in this model system. Accordingly, the disclosure provides methods of reducing, delaying the onset of, or ameliorating one or more pathophysiological characteristics of Alzheimer's disease, such as neuronal cell apoptosis, neuroinflammation, beta-amyloid burden, and tau protein hyperphosphorylation.

The present invention is also based, in part, on the finding that igmesine is able to prevent the appearance of learning and memory deficits elicited by $A\beta_{25\text{-}35}$ induced neurotoxicity and which are associated with both spatial working memory and contextual long-term memory. Accordingly, the disclosure provides methods of reducing, delaying the onset of, or ameliorating at least one clinical symptom of Alzheimer's disease, such as a learning or memory deficit associated with one or more of working memory, short term memory, long term memory, positively reinforced memory, a spatial and contextual memory, or any combination of the foregoing.

The present invention is also based, in part, on the finding that the neuroprotective effects of igmesine were manifested in a dosage range that was on the order of 10 to 100-fold lower than the effective dose range previously observed in humans, for example, in connection with its anti-depressant effects, and in rodents, for example, in connection with its neuroprotective effects in models of global cerebral ischemia. Accordingly, the disclosure provides methods and related compositions for treating a neurological disease or disorder using an effective dose of igmesine that is 10 to 100-fold lower than the doses previously utilized in, e.g., phase I clinical studies of igmesine.

In addition, the present invention is based, in part, on the finding that igmesine acts synergistically with other therapeutic agents to prevent or substantially reduce $A\beta_{25\text{-}35}$ induced neurotoxicity. Accordingly, the disclosure provides methods and related compositions for treating Alzheimer's disease using igmesine in combination with one or more additional therapeutic agents. In embodiments, the Alzheimer's disease is early onset disease. In embodiments, the one or more additional therapeutic agents is selected from the group consisting of a cholinesterase inhibitor, a MAO inhibitor, an anti-inflammatory agent, an Aβ toxicity lowering agent, a hormone replacement agent, a lipid-lowering agent, a secretase modulating agent, an Aβ aggregation inhibitor, a neurofibrillary inhibitor, a β-amyloid amyloid catabolism inhibitor, and combinations thereof.

In further embodiments for the treatment of Alzheimer's disease, the one or more additional therapeutic agents is selected from a cholinesterase inhibitor, an anti-inflammatory agent, a lipid-lowering agent, and a MAO inhibitor. In embodiments, the cholinesterase inhibitor is donepezil. In embodiments, the amount of the donepezil in the composition is from 1 to 6 mg. In embodiments, the anti-inflammatory agent is a steroidal or non-steroidal anti-inflammatory agent. In one embodiment, the anti-inflammatory agent is ibuprofen or aspirin.

In embodiments, the one or more additional therapeutic agents is a lipid-lowering agent. In embodiments, the lipid-lowering agent is a statin. In embodiments, the statin is selected from the group consisting of atorvastatin, risuvostatin, simvastatin, pravastatin, and pharmaceutically acceptable salts or prodrugs thereof. In one embodiment, the statin is simvastatin or atorvastatin.

In embodiments, the one or more additional therapeutic agents is a MAO inhibitor. In embodiments, the MAO inhibitor is selected from rasagiline, selegiline and tranylcypromine. In embodiments, the MAO inhibitor is a MAO-B inhibitor. In embodiments, the MAO-B inhibitor is selegiline.

The present invention is also based, in part, on the ability of igmesine to reduce or prevent neuronal cell apoptosis and further on the ability of igmesine to promote the chaperone activity of sigma-1 receptors and thereby attenuating the accumulation of misfolded proteins that underlie disease pathology. Accordingly, the present disclosure provides compositions and methods for treating a neurodegenerative disease or disorder using igmesine, either alone as monotherapy, or in combination with one or more additional therapeutic agents or therapeutic regimens, as described herein. In embodiments, the neurodegenerative disease or disorder may be selected from Alzheimer's disease, amyotrophic lateral sclerosis (ALS), Huntington's disease, multiple sclerosis, Parkinson's disease and frontotemporal degeneration. In embodiments, the neurodegenerative disease or disorder is Alzheimer's disease. In embodiments, the Alzheimer's disease is early onset disease.

In embodiments of the therapeutic methods described herein, igmesine is administered at a therapeutically effective dose of from 1 to 100 mg, from 1 to 50 mg, from 1 to 20 mg, from 1 to 10 mg, or from 1 to 5 mg per day in an adult human subject having a weight of about 70 kg. Preferably, the route of administration for the dosage is oral, and most preferably the dosage form is adapted for once-daily delivery of the effective dose.

As discussed in more detail infra, the disclosure also provides pharmaceutical compositions comprising igmesine and one or more additional therapeutic agents, in the presence of one or more pharmaceutically acceptable excipients. In embodiments, the igmesine is present in the same dosage form as the one or more additional therapeutic agents. In embodiments, the igmesine is present in a different dosage form from the one or more additional therapeutic agents. The disclosure also provides a unit dosage form containing igmesine, either alone or in combination with one or more additional therapeutic agents. In embodiments, the unit dose contains from 1 to 100 mg, from 1 to 50 mg, from 1 to 20 mg, from 1 to 10 mg, from 1 to 5 mg, or from 3 to 10 mg of igmesine, preferably igmesine hydrochloride.

As used throughout the present disclosure, the term "igmesine" may refer to igmesine itself (free base), or may encompass pharmaceutically acceptable salts, solvates, clathrates, hydrates, polymorphs, prodrugs, analogs or derivatives of igmesine, as described below. In any of the embodiments of the methods and compositions described here, a preferred embodiment of igmesine is igmesine hydrochloride. Igmesine contains an asymmetric tetrasubstituted carbon atom adjacent to the amine function, which results in the existence of racemic, laevorotatory and dextrorotatory forms. Unless otherwise indicated, the term "igmesine" refers to the dextrorotatory (+) enantiomer identified as JO-1784 or AMY002.

The structure of igmesine free base is shown below:

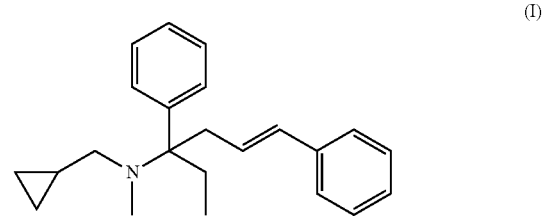 [SMILES: CCC(C/C=C/c1ccccc1)(c1ccccc1)N(C)CC1CC1]

(I)

The IUPAC name of igmesine is: (+)-(E)-N-(cyclopropylmethyl)-N-methyl-3,6-diphenylhex-5-en-3-amine and the CAS number is 140850-73-3 (which is the free base of the (+) enantiomer).

Igmesine is commercially available and can be prepared, for example, according to the methods described in U.S. Pat. No. 5,034,419, which also describes the pharmaceutically acceptable salts, solvates, clathrates, hydrates, polymorphs, prodrugs, analogs and derivatives of igmesine.

As used herein, the term "pharmaceutically acceptable salt," is a salt formed, for example, by acid addition with the amine function of igmesine. Non-limiting examples of acids which may be used to prepare such addition salts include acetic, benzensulphonic, camphosulphonic, citric, ethanesulphonic, fumaric, hydrobromic, hydrochloric, lactic, maleic, malic, methanesulphonic, mucic, nitric, pamoic, phosphoric, salicylic, stearic, succinic, sulphuric and tartaric acids.

The salts of igmesine can be synthesized from the parent compound by conventional chemical methods such as methods described in Pharmaceutical Salts: Properties, Selection, and Use, P. Hemrich Stahl (Editor), Camille G. Wermuth (Editor), ISBN: 3-90639-026-8, August 2002. Generally, such salts can be prepared by reacting the parent compound with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid using routine methods.

The term "polymorph" refers to solid crystalline forms of a compound (e.g., igmesine) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "hydrate" refers to a compound (e.g., igmesine) or a salt thereof, which further includes a stoichiometric or non-stoichiometric amount of water bound by non-covalent intermolecular forces.

The term "clathrate" refers to a compound (e.g., igmesine) or a salt thereof in the form of a crystal lattice that contains spaces (e.g., channels) that have a guest molecule (e.g., a solvent or water) trapped within.

The term "prodrug" refers to a derivative of a compound described herein (e.g., igmesine) that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein (e.g., igmesine) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs can typically be prepared using well-known methods, such as those described by Burger's Medicinal Chemistry and Drug Discovery (1995) 172-178, 949-982 (Manfred E. Wolff ed., $5^{th}$ ed.).

The term "solvate" or "pharmaceutically acceptable solvate," refers to a solvate formed from the association of one or more solvent molecules to one of the compounds disclosed herein (e.g., igmesine). The term solvate includes hydrates (e.g., hemi-hydrate, mono-hydrate, dihydrate, trihydrate, tetrahydrate, and the like).

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The present disclosure provides methods for the treatment of a neurological disease or disorder in a subject in need thereof by administering to the subject a therapeutically effective amount of a composition comprising igmesine, or a pharmaceutically acceptable salt, solvate, clathrate, hydrate, polymorph, prodrug, analog or derivative thereof. In one embodiment, the composition comprises igmesine hydrochloride. The present invention further provides for the use of igmesine for the preparation of a medicament useful for the treatment of a neurological disease or disorder, as described herein.

In the context of the methods described herein, the amount of igmesine administered to the subject is a therapeutically effective amount. The term "therapeutically effective amount" refers to an amount sufficient to treat, ameliorate a symptom of, reduce the severity of, delay the onset of, one or more clinical symptoms of the neurological disease or disorder in the subject being treated, or to enhance or improve the therapeutic effect of another therapy, or ameliorate or delay the onset of one or more pathophysiological characteristics of the disease or disorder. In embodiments, the therapeutically effective amount of igmesine is from 1 to 100 mg, from 1 to 50 mg, from 1 to 20 mg, from 1 to 10 mg, or from 1 to 5 mg per day in an adult human weighing 70 kg. The preferred route of administration is oral.

In accordance with the methods described herein, a "subject in need of" is a subject having been diagnosed with a neurological disease or disorder. In embodiments, the neurological disease or disorder is selected from Alzheimer's disease, early onset Alzheimer's disease, amyotrophic lateral sclerosis, multiple sclerosis, Parkinson's disease, Huntington's disease, and frontotemporal degeneration.

Combination Therapy

The present disclosure also provides methods comprising combination therapy. As used herein, "combination therapy" or "co-therapy" includes the administration of a therapeutically effective amount of igmesine with at least one additional active agent, as part of a specific treatment regimen intended to provide a beneficial effect from the co-action of the igmesine and the additional active agent. "Combination therapy" is not intended to encompass the administration of two or more therapeutic compounds as part of separate monotherapy regimens that incidentally and arbitrarily result in a beneficial effect that was not intended or predicted.

The at least one additional active agent may be a therapeutic agent, or a non-therapeutic agent, and combinations thereof. The terms "therapeutic agent" and "active pharmaceutic ingredient ("API") are used interchangeably herein. With respect to therapeutic agents, the beneficial effect of the combination includes, but is not limited to, pharmacokinetic or pharmacodynamic co-action resulting from the combination of therapeutically active compounds. With respect to non-therapeutic agents, the beneficial effect of the combination may relate to the mitigation of a toxicity, side effect, or adverse event associated with a therapeutic agent in the combination.

In embodiments, the at least one additional agent is a non-therapeutic agent which mitigates one or more side effects of igmesine or a second API included in the composition. The one or more side effects may be selected from any of nausea, vomiting, headache, dizziness, lightheadedness, drowsiness and stress.

In embodiments, the therapeutic agent or API is a cholinesterase inhibitor, an anti-inflammatory agent, a MAO inhibitor, an NMDA receptor antagonist, an Aβ toxicity lowering agent, a hormone replacement agent, a lipid-lowering agent, a secretase modulating agent, an Aβ aggregation inhibitor, a neurofibrillary inhibitor, or a β-amyloid catabolism inhibitor. In embodiments, the therapeutic agent or API is a cholinesterase inhibitor, an anti-inflammatory agent, a MAO inhibitor, or a lipid-lowering agent.

In accordance with any of the embodiments described here relating to the treatment of Alzheimer's disease, the cholinesterase inhibitor may be selected from the group consisting of physostigmine, neostigmine, pyridostigmine, ambenonium, demecarium, rivastigmine, galantamine, donepezil, tacrine (tetrahydroaminoacridine), edrophonium, huperzine A, ladostigil, ungeremine, and lactucopicrin. In embodiments, the cholinesterase inhibitor is donepezil.

In embodiments, the cholinesterase inhibitor is selected from the group consisting of tacrine, amiridine, donepezil and its derivatives TAK-147 and CP-118'954, minaprine, rivastigmine, galantamine, huperzine, huprine, bis-tetrahydroaminoacridine (bis-THA) and its derivatives such as bis (7)-tacrine, imidazoles, 1,2,4-thiadiazolidinone, benzazepine derivatives, 4,4-bipyridine indenoquinolinylamine, decamethonium, edrophonium, BW284C51, physostigmine, eptastigmine, metrifonate, propidium, fasciculins, organophosphates, carbamates, imino 1,2,3,4-tetrahydrocyclopent [b]indole carbamates (hybrids of the AChE inhibitor physostigmine and MAO inhibitor selegiline and tranylcypropmine), N-Pyrimidine 4-acetylaniline derivatives, 7-aryloxycoumarin derivatives, propargyiamino carbamates such as N-propargylaminoindans and N-propargylphenethylamines, vitamin E, NOS inhibitors, precursors such as choline and pyrrolidinecholine, and cholinergic receptor agonists (e.g. nicotinic, particularly α7 and muscarinic).

In accordance with any of the embodiments described here relating to the treatment of Alzheimer's disease, the anti-inflammatory agent may be a steroidal or non-steroidal anti-inflammatory agent. In embodiments, the anti-inflammatory agent is selected from the group consisting of adrenocorticoids, corticosteroids (e.g., beclomethasone, budesonide, flunisolide, fluticasone, triamcino lone, methylpredniso lone, predniso lone, prednisone, hydrocortisone), glucocorticoids, and steroids. In embodiments, the non-steroidal anti-inflammatory agent is selected from the group consisting of aspirin, ibuprofen, diclofenac, and COX-2 inhibitors. In embodiments, the anti-inflammatory agent is selected from leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC).

In accordance with any of the embodiments described here relating to the treatment of Alzheimer's disease, the MAO inhibitor may be selected from rasagiline, selegiline and tranylcypromine. In embodiments, the MAO inhibitor is a MAO-B inhibitor. In embodiments, the MAO-B inhibitor is selegiline.

In accordance with any of the embodiments described here relating to the treatment of Alzheimer's disease, the hormone replacement agent may be selected from prefest, premarin, vivelle, estrasorb, enjuvia, delestrogen, climara, and alora.

In accordance with any of the embodiments described here relating to the treatment of Alzheimer's disease, the Aβ toxicity lowering agent may be selected from a nonsteroidal anti-inflammatory drug, a death associated protein kinase (DAPK) inhibitor (e.g., derivatives of 3-amino pyridazine), a cyclooxygenases (COX-1 and -2) inhibitor, an antioxidant (e.g., vitamins C and E), a modulator of NMDA (e.g., memantine), and a MAO inhibitor (e.g., rasagiline, selegiline and tranylcypromine). In embodiments, the agent is a nonsteroidal anti-inflammatory drug selected from ibuprofen, indomethacin and sulindac sulfide.

In accordance with any of the embodiments described here relating to the treatment of Alzheimer's disease, the lipid-lowering agent may be selected from 3-hydroxy-3-methylglutaryl coenzyme A (HMG-CoA) reductase inhibitors and statins. In embodiments, the agent is selected from methyl-β-cyclodextrin, 7-dehydrocholesterol reductases (e.g. BM15.766), acyl co-enzyme A:cholesterol acyltransferase (ACAT) inhibitors, P13K inhibitors such as wortmannin, lovastatin, pravastatin, atorvastatin, simvastatin, fluvastatin, cerivastatin, rosuvastatin, compactin, mevilonin, mevastatin, visastatin, velostatin, synvinolin, rivastatin, itavastatin, and pitavastatin.

In accordance with any of the embodiments described here relating to the treatment of Alzheimer's disease, the secretase inhibitor may be selected from inhibitors of β- and γ-secretase. In embodiments, the secretase inhibitor is selected from the group consisting of tripeptide aldehyde 1, SIB-1281, OM99-2, Stat-Val, alkoxy substituted tetralins, difluoroketone-based compounds, SIB-1405, hydroxy substituted peptide urea, alanine-phenylglycine derivatives, caprolactams, benzodiazepines and hexanamides, enchylamine sulfonamide, bicyclic sulfonamide and isocoumarin, sulfonamide, diaryl acetylene, imidazopyridine and polyoxygenated aromatci structures, protein kinase C activators, glutamate, carbachol, muscarinic agonists, AIT-082

(Neotrophin™), neurotrophic agents, copper (II) containing compounds and cholesterol depleting agents.

In accordance with any of the embodiments described here relating to the treatment of Alzheimer's disease, Aβ aggregation inhibitors may be selected from peptidyl inhibitors (e.g. pentapeptide inhibitors), analogs of the amyloid binding dyes Congo red and thioflavin T, analogs of the anti-cancer agent doxorubicin (e.g. anthracycline-4'-deoxy-4'-iododoxcorubicin (IDOX)), antibodies such as rifampicin or analogs thereof and clioquinol, benzofurans (e.g. SKF-74652), inhibitors of serum amyloid protein (SAP) such as captopril (e.g. CPHPC), and metal chelation by addition of Cu2+, ZN2+ or Fe3+.

In accordance with any of the embodiments described here relating to the treatment of Alzheimer's disease, the neurofibrillary inhibitor may be selected from GSK3β inhibitors such as LICI, GSK3β and cdk5 inhibitors such as indirubins and paulones, and calpain inhibitors.

In embodiments, a composition comprising igmesine is administered along with the at least one additional active agent in a single dosage form or in separate dosage forms. In one embodiment, the dosage form is an oral dosage form. In another embodiment, the dosage form is suitable for intravenous administration.

In the context of combination therapy, administration of the igmesine may be simultaneous with or sequential to the administration of the one or more additional active agents. In another embodiment, administration of the different components of a combination therapy may be at different frequencies. The one or more additional active agents can be formulated for co-administration with igmesine in a single dosage form, as described in greater detail herein. The one or more additional active agents can be administered separately from the dosage form that comprises the compound of the present invention. When the additional active agent is administered separately from the igmesine composition, it can be by the same or a different route of administration as the igmesine composition.

Preferably, the administration of igmesine in combination with one or more additional agents provides a synergistic response in the subject being treated. In this context, the term "synergistic" refers to the efficacy of the combination being more effective than the additive effects of either single therapy alone. The synergistic effect of a combination therapy according to the invention can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present invention in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In accordance with any of the methods described herein, a therapeutically effective amount of igmesine, e.g., igmesine hydrochloride, can range from about 1 to 100 mg, from about 1 to 50 mg, or from about 1 to 20 mg per unit dose for an adult human, preferably administered once or twice daily, most preferably administered once daily. In embodiments, the therapeutically effective amount of igmesine is from 1 to 20 mg, from 1 to 15 mg, from 1 to 10 mg, from 1 to 5 mg, from 1 to 3 mg, or from 1 to 2 mg.

In embodiments where igmesine is combined with a cholinesterase inhibitor, a lower dose range of igmesine is generally effective. For example, the therapeutically effective amount of igmesine in combination with donepezil may be from 1 to 10 mg, from 1 to 8 mg, from 1 to 6 mg, from 1 to 5 mg, from 1 to 4 mg, from 1 to 3 mg, or from 1 to 2 mg, per day.

Effective doses will also vary, as recognized by those skilled in the art, depending on the diseases treated, route of administration, excipient usage, and the possibility of co-usage with other therapeutic treatments such as use of other agents.

A therapeutically effective amount of the igmesine is preferably administered once or twice daily. The preferred route of administration is oral, but other routes are contemplated and the skilled person may readily calculate the appropriate dose for other routes based upon the guidance herein using standard methods.

A "subject" as used in the context of the methods described herein is preferably a human subject but may also include other mammals. The mammal can be e.g., any mammal, e.g., a human, primate, vertebrate, bird, mouse, rat, fowl, dog, cat, cow, horse, goat, camel, sheep or a pig. The term "patient" refers to a human subject.

The present invention also provides a monotherapy for the treatment of a neurological disease or disorder as described herein. As used herein, "monotherapy" refers to the administration of a single active agent (also referred to as the therapeutic agent), e.g., igmesine, and in embodiments, igmesine hydrochloride, to a subject in need thereof.

As used herein, "treatment", "treating" or "treat" describes the management and care of a patient for the purpose of combating the disease or disorder and includes alleviating one or more symptoms or complications of the disease or disorder.

In embodiments, the administration of a composition as described herein leads to the elimination of a symptom or complication of the disease or disorder being treated, however, elimination is not required. In one embodiment, the severity of the symptom is decreased, or its onset is delayed, or both.

Pharmaceutical Compositions and Formulations

The present invention provides pharmaceutical compositions comprising igmesine, or a pharmaceutically acceptable salt, solvate, clathrate, hydrate, polymorph, prodrug, analog or derivative thereof. The pharmaceutical compositions are suitable for use in a mammal, preferably a human. In this context, the compositions may further comprise at least one pharmaceutically acceptable excipient or carrier. In embodiments, the compositions comprise an effective amount of igmesine, wherein the amount is effective for the treatment of a neurological disease or disorder. The effective amount of igmesine per unit dose for an oral composition intended for an adult human subject is generally less than 20 mg or less than 10 mg, and generally in the range of from about 1 to 20 mg, preferably 1 to 10 mg. As described supra, where the composition comprises igmesine and an additional API, such as a cholinesterase inhibitor, the amount of igmesine in the composition may be in the low end of its effective dose range, e.g., from 1 to 10 mg, preferably from 1 to 5 mg, or less than 5 mg.

In embodiments, the igmesine composition comprises igmesine hydrochloride.

In embodiments, the igmesine composition is combined with at least one API in a single dosage form. In embodiments, the at least one additional API is selected from the group consisting of a cholinesterase inhibitor, an Aβ toxicity lowering agent, a hormone replacement agent, a lipid-lowering agent, a secretase modulating agent, an Aβ aggregation inhibitor, a neurofibrillary inhibitor and a β-amyloid catabolism inhibitor. In embodiments, one or more additional therapeutic agents is a cholinesterase inhibitor.

In embodiments, the cholinesterase inhibitor may be selected from the group consisting of physostigmine, neostigmine, pyridostigmine, ambenonium, demecarium, rivastigmine, galantamine, donepezil, tacrine (tetrahydroaminoacridine), edrophonium, huperzine A, ladostigil, ungeremine, and lactucopicrin. In embodiments, the cholinesterase inhibitor is donepezil.

In embodiments, the hormone replacement agent may be estrogen or an estrogenic compound. In embodiments, the hormone replacement agent may be selected from the hormone replacement agent may be selected from prefest, premarin, vivelle, estrasorb, enjuvia, delestrogen, climara, and alora.

In embodiments, the Aβ toxicity lowering agent may be selected from a nonsteroidal anti-inflammatory drug, a death associated protein kinase (DAPK) inhibitor (e.g., derivatives of 3-amino pyridazine), a cyclooxygenases (COX-1 and -2) inhibitor, an antioxidant (e.g., vitamins C and E), a modulator of NMDA (e.g., memantine), and a MAO inhibitor (e.g., rasagiline, selegiline and tranylcypromine). In embodiments, the agent is a nonsteroidal anti-inflammatory drug selected from ibuprofen, indomethacin and sulindac sulfide.

In embodiments, the lipid-lowering agent may be selected from 3-hydroxy-3-methyglutaryl coenzyme A (HMG-CoA) reductase inhibitors and statins. In embodiments, the agent is selected from methyl-β-cyclodextrin, 7-dehydrocholesterol reductases (e.g. BM15.766), acyl co-enzyme A:cholesterol acyltransferase (ACAT) inhibitors, P13K inhibitors such as wortmannin, lovastatin, pravastatin, atorvastatin, simvastatin, fluvastatin, cerivastatin, rosuvastatin, compactin, mevilonin, mevastatin, visastatin, velostatin, synvinolin, rivastatin, itavastatin, and pitavastatin.

In embodiments, the secretase inhibitor may be selected from inhibitors of β- and γ-secretase. In embodiments, the secretase inhibitor is selected from the group consisting of tripeptide aldehyde 1, SIB-1281, OM99-2, Stat-Val, alkoxy substituted tetralins, difluoroketone-based compounds, SIB-1405, hydroxy substituted peptide urea, alanine-phenylglycine derivatives, caprolactams, benzodiazepines and hexanamides, enchylamine sulfonamide, bicyclic sulfonamide and isocoumarin, sulfonamide, diaryl acetylene, imidazopyridine and polyoxygenerated aromatci structures, protein kinase C activators, glutamate, carbachol, muscarinic agonists, AIT-082 (Neotrophin™), neurotrophic agents, copper (II) containing compounds and cholesterol depleting agents.

In embodiments, Aβ aggregation inhibitors may be selected from peptidyl inhibitors (e.g. pentapeptide inhibitors), analogs of the amyloid binding dyes Congo red and thioflavin T, analogs of the anti-cancer agent doxorubicin (e.g. anthracycline-4'-deoxy-4'-iododoxcorubicin (IDOX)), antibodies such as rifampicin or analogs thereof and clioquinol, benzofurans (e.g. SKF-74652), inhibitors of serum amyloid protein (SAP) such as captopril (e.g. CPHPC), and metal chelation by addition of Cu2+, ZN2+ or Fe3+.

In embodiments, the neurofibrillary inhibitor may be selected from GSK3β inhibitors such as LICl, GSK3β and cdk5 inhibitors such as indirubins and paulones, and calpain inhibitors.

In embodiments, the at least one additional active agent is a non-therapeutic agent selected to ameliorate one or more side effects of igmesine or the additional API.

A "pharmaceutical composition" is a formulation containing the compounds described herein in a pharmaceutically acceptable form suitable for administration to a subject, preferably a human subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The specifications for the unit dosage forms of the invention are dictated by and directly dependent on the unique characteristics of the active compound and the particular therapeutic effect to be achieved. A unit dosage form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

In embodiments, the unit dosage form may comprise from 1 to 20 mg or from 1 to 10 mg of igmesine, or a pharmaceutically acceptable salt thereof. In embodiments, the unit dose contains 1, 2, 3, 4, 5, 6, 7, 8, 9, or 10 mg of igmesine.

In embodiments, the unit dose contains 12, 15, or 20 mg of igmesine, or a pharmaceutically acceptable salt thereof.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose); in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a neurological disease, condition or disorder as described herein, one or more syringes, one or more applicators, or a sterile solution suitable for reconstituting a pharmaceutical composition of the present invention.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

ER stress has been shown to cause the rapid upregulation of sigma-1 receptors and sigma-1 receptors are reported to be downregulated in the putamen of patients in the early stage of Parkinson's disease as well as in brains of Alzheimer's disease patients (Jansen K L, et al. 1993. *Brain Res.* 623(2): 299-302; Mishina M, et al. 2005. *Acta neurologica Scandinavica* 112(2): 103-107; Toyohara J, et al. 2009. *Central nervous system agents in medicinal chemistry* 9(3): 190-196). Lowered sigma-1 receptor levels seen in these subjects might raise susceptibility of the brain to ER stress. Sigma-1 agonists that increase the innate chaperone activity of sigma-1 receptors may thus exert therapeutic potential in treating neurological diseases where ER stress is implicated in the pathophysiology. Overproduction of free radicals is also strongly implicated in the pathophysiology of neurodegenerative disorders as substantiated by findings that protein side-chains are modified either by ROS or reactive nitrogen species (RNS), or by the products of lipid peroxidation in brain tissue of patients who have died of these disorders. For example, in brains of Alzheimer's disease patients, iron ($Fe^{2+}$) and copper ($Cu^{2+}$) are increased (Jomova K, et al. 2010. *Mol. Cell. Biochem.* 345(1-2): 91-104). Both of these cations are capable of stimulating free radical formation. Collectively, recent findings suggest that the primary action of sigma-1 chaperones may be to regulate ER stress and mitochondrial function. However, the regulation of the two intracellular organelles and their communications seem to greatly contribute to the suppression of ROS and oxidative stress. As a consequence, ROS-related downstream signals that include many gene transcripts work collaboratively toward prevention of apoptosis and inflammation.

Accordingly, we investigated whether or not igmesine was effective in a mouse model of acute Alzheimer's disease. Prior to the present study, no studies have reported an effect of igmesine on such hallmarks of disease pathology as neuroinflammation, neuronal cell apoptosis, amyloid plaque burden, tau protein hyperphosphorylation, or oxidative stress. As discussed below, the results presented here demonstrate that igmesine treatment was able to effectively prevent the development of these disease features, even where treatment with igmesine was initiated 24 hours after exposure to the neurotoxicity inducing $A\beta_{25-35}$ peptide. The neuroprotective effects of igmesine against the development of the disease related features in this model system is demonstrated by the normalization of both memory performance in treated animals and neuronal biochemical parameters.

Importantly, the protective effects of igmesine were found over a surprisingly low dose range of about 0.1 to 1 mg/kg in the mouse. This effective dose is well below that required for igmesine's anti-depressant effects, which was in the range of 30-60 mg/kg in the mouse. In addition, we show that igmesine acted synergistically with the cholinesterase inhibitor donepezil, enabling donepezil to exhibit its therapeutic effects in a dosage range that was 4-fold lower than the typical therapeutically effective range, which is 5 to 23 mg/day in the treatment of Alzheimer's disease in humans. Similar synergistic effects are shown here with the monoamine oxidase-B inhibitor, selegiline, the non-steroidal anti-inflammatory compound, ibuprofen, and the lipid lowering agent, atorvastatin. The observed synergism with igmesine permitted the use of each of ibuprofen and selegiline at doses at 3-fold lower and atorvastatin at doses 10-fold lower than the usual doses of each that are generally prescribed for their primary indications. Accordingly, these results indicate that igmesine in combination with each of these agents may provide new treatment regimens for AD which, by virtue of the low doses of both igmesine and these additional agents, is expected to increase efficacy while decreasing systemic side effects associated with this agents when they are used at higher doses, thereby raising the therapeutic index of these drugs when used in combination therapy as described herein.

Based upon the results described here, we estimate the effective dose range in humans as follows. In phase I studies of igmesine conducted in connection with its anti-depressive activity, the effective doses were 25 mg and 100 mg per day. Taking into account the much higher efficacy (shift of 100-fold) observed in mice in Example 1, we estimate the effective doses for neuroprotection using igmesine alone (as monotherapy) to be in the range of about 2.5 mg to 10 mg in a human of average weight (about 70 kg), or about 0.035 mg/kg to 0.14 mg/kg a day. The doses of donepezil follow a similar calculation, as usual doses in human are 5, 10 and 23 mg/day and the efficacy is 4-fold higher when associated with igmesine. Accordingly, we expect the effective dose of donepezil in combination with igmesine to be in the range of from 1 to 15 mg/day, preferably about 1, 2, 3, or 4 mg/day.

Example 1

Neuroprotective Effects of Igmesine in the $A\beta_{25-35}$ Mouse Model of Alzheimer's Disease The following demonstrates that igmesine, but not memantine, displays neuroprotective effects in the $A\beta_{25-35}$ mouse model of Alzheimer disease (AD). The results show that at doses 100-fold lower than the doses active in depression, igmesine is able to protect animals from learning/memory deficits and profound biochemical alterations of brain tissue produced by the intracerebroventricular (i.c.v) injection of $A\beta_{25-35}$ toxic peptide. This protective effect was observed when igmesine is administered as a preventive acute treatment (i.e., 20 min before the peptide injection) but also as a chronic curative treatment starting 1 day after the injection of the peptide and stopping 1 day before the memory tests. These results demonstrate that igmesine is acting as a neuroprotectant able to protect neurons from the toxic effects of the peptide and not merely as a memory enhancer. The results presented here suggest that igmesine could benefit patients in the early stages of Alzheimer's disease, or those considered at high risk of developing the disease, by slowing or even stopping the progression of the disease pathology.

The purpose of the study was to determine whether igmesine (AMY-002) can alleviate the pathology induced in mice injected intracerebroventricularly (i.c.v) with oligomeric amyloid-$\beta_{25-35}$ peptide ($A\beta_{25-35}$) and to determine whether the drug could induce synergistic effects with other reference drugs, acetylcholinesterase inhibitor (AChEI) donepezil (Aricept®), the NMDA receptor antagonist memantine (Ebixa®), the MAO-B inhibitor selegiline (Deprenyl), the non-steroidal anti-inflammatory drug (NSAID) ibuprofen (Advil) or the 3-hydroxy-3-methylglutaryl coenzyme A (HMG CoA) reductase inhibitor atorvastatin (Lipitor).

The compound efficacy was evaluated 7 days after the peptide administration on the attenuation of the $A\beta_{25-35}$-induced learning deficits (spatial working memory using the spontaneous alternation in the Y-maze test, and contextual long-term memory using the passive avoidance test).

In Experiment 1, twelve mice per experimental group were administered igmesine, donepezil or vehicle i.p. 20 min before i.c.v. injection of $A\beta_{25-35}$ or scrambled peptide (Sc.A$\beta$). The mice were tested 7 days post injection or at the indicated time points.

In Experiment 2, twelve mice per experimental group were administered Sc.A$\beta$ or $A\beta_{25-35}$-amyloid peptide on day 0 by i.c.v. injection. Igmesine, donepezil or vehicle was administered i.p. from day 1 to day 6 after $A\beta_{25-35}$ injection. Animals were tested at day 7 and later.

In Experiment 3, twelve mice per experimental group were administered Sc.A$\beta$ or $A\beta_{25-35}$-amyloid peptide by i.c.v. injection 20 minutes prior to i.p injection. with two different doses of each of igmesine (0.1 mg/kg and 0.3 mg/kg), donepezil (0.25 mg/kg and, 0.5 mg/kg) and memantine (0.5 mg/kg and, 1 mg/kg). The lowest dose combinations were also tested: igmesine 0.1 mg/kg+donepezil 0.25 mg/kg or igmesine 0.1 mg/kg+memantine 0.5 mg/kg, to determine the synergistic effect of the drugs in neuroprotection. Each of these doses was, by itself, unable to produce any protective effect. The synergy/additivity/antagonism was evaluated by calculating the combination index. On day 0, igmesine, donepezil, memantine, each combination or the vehicle solution was injected i.p., 20 min before i.c.v. injection and every day up to day 7. Animals were then tested at day 7 and later.

In Experiment 4, twelve mice were administered igmesine or vehicle and six mice were administered ibuprofen (25 mg/kg), selegiline (1 mg/kg) or and atorvastatin (1 mg/kg) in combination with a low dose of igmesine (0.1 mg/kg) starting 24 h after $A\beta_{25-35}$ injection (day 1) and every day up to day 6 as in the experiment 2. Animals were tested at day 7 and later. At the doses tested here, all compounds were unable by themselves to produce any protective effect.

For each of Experiments 1-4, on day 7, all animals were tested for the spontaneous alternation performance in the Y-maze test, an index of spatial working memory. On day 8 and 9, the contextual long-term memory of the animals was assessed using the step-through type passive avoidance procedure. On day 9, immediately after the retention session, animals were sacrificed by decapitation and the hippocampus and cortex dissected out. Lipid peroxidation was analyzed in the hippocampus, whereas neuroinflammation, apoptosis, amyloid burden and hyperphosphorylation of tau protein were analyzed in cortex.

TABLE 1

Treatment groups in experiment 1.

| | n |
|---|---|
| 1. Sc.A$\beta$ + Vehicle solution | 12 |
| 2. Sc.A$\beta$ + igmesine (1 mg/kg IP) | 12 |
| 3. $A\beta_{25-35}$ + Vehicle solution | 12 |
| 4. $A\beta_{25-35}$ + igmesine (0.1 mg/kg IP) | 12 |
| 5. $A\beta_{25-35}$ + igmesine (0.3 mg/kg IP) | 12 |
| 6. $A\beta_{25-35}$ + igmesine (1 mg/kg IP) | 12 |
| 7. $A\beta_{25-35}$ + donepezil (1 mg/kg IP) | 12 |
| Total mice | 84 |

TABLE 2

Treatment groups in experiment 2.

| | n |
|---|---|
| 1. Sc.A$\beta$ + Vehicle solution | 12 |
| 2. Sc.A$\beta$ + igmesine (1 mg/kg IP) | 12 |
| 3. $A\beta_{25-35}$ + Vehicle solution | 12 |
| 4. $A\beta_{25-35}$ + igmesine (0.1 mg/kg IP) | 12 |
| 5. $A\beta_{25-35}$ + igmesine (0.3 mg/kg IP) | 12 |
| 6. $A\beta_{25-35}$ + igmesine (1 mg/kg IP) | 12 |
| 7. $A\beta_{25-35}$ + donepezil (1 mg/kg IP) | 12 |
| Total mice | 84 |

TABLE 3

Treatment groups in experiment 3.

| | n |
|---|---|
| 1. Sc.A$\beta$ + Vehicle solution | 12 |
| 2. $A\beta_{25-35}$ + Vehicle solution | 12 |
| 3. $A\beta_{25-35}$ + igmesine (0.1 mg/kg IP) | 12 |
| 4. $A\beta_{25-35}$ + igmesine (0.3 mg/kg IP) | 12 |
| 5. $A\beta_{25-35}$ + donepezil (0.25 mg/kg IP) | 12 |
| 6. $A\beta_{25-35}$ + donepezil (0.5 mg/kg IP) | 12 |
| 7. $A\beta_{25-35}$ + memantine (0.5 mg/kg IP) | 12 |
| 8. $A\beta_{25-35}$ + memantine (1 mg/kg IP) | 12 |
| 9. $A\beta_{25-35}$ + igmesine (0.1 mg/kg IP) + donepezil (0.25 mg/kg IP) | 12 |
| 10. $A\beta_{25-35}$ + igmesine (0.1 mg/kg IP) + memantine (0.5 mg/kg IP) | 12 |
| Total mice | 120 |

TABLE 4

Treatment groups in experiment 4.

| | n |
|---|---|
| 1. Sc.A$\beta$ + Vehicle solution | 12 |
| 2. $A\beta_{25-35}$ + Vehicle solution | 12 |

TABLE 4-continued

Treatment groups in experiment 4.

| | n |
|---|---|
| 3. Aβ$_{25-35}$ + igmesine (0.1 mg/kg IP) | 12 |
| 4. Aβ$_{25-35}$ + ibuprofen (25 mg/kg IP) | 6 |
| 5. Aβ$_{25-35}$ + ibuprofen (50 mg/kg IP) | 6 |
| 6. Aβ$_{25-35}$ + igmesine (0.1 mg/kg IP) + ibuprofen (25 mg/kg IP) | 6 |
| 7. Aβ$_{25-35}$ + igmesine (0.1 mg/kg IP) + ibuprofen (50 mg/kg IP) | 6 |
| 8. Aβ$_{25-35}$ + selegiline (1 mg/kg IP) | 6 |
| 9. Aβ$_{25-35}$ + selegiline (3 mg/kg IP) | 6 |
| 10. Aβ$_{25-35}$ + selegiline (10 mg/kg IP) | 6 |
| 11. Aβ$_{25-35}$ + igmesine (0.1 mg/kg IP) + selegiline (3 mg/kg IP) | 6 |
| 12. Aβ$_{25-35}$ + atorvastatin (0.25 mg/kg IP) | 6 |
| 13. Aβ$_{25-35}$ + atorvastatin (0.75 mg/kg IP) | 6 |
| 14. Aβ$_{25-35}$ + atorvastatin (2.5 mg/kg IP) | 6 |
| 15. Aβ$_{25-35}$ + igmesine (0.1 mg/kg IP) + atorvastatin (0.75 mg/kg IP) | 6 |
| Total mice | 108 |

Igmesine (AMY002), donepezil, memantine, ibuprofen, selegiline and atorvastatin were from commercial sources. Upon receipt, the drug and accompanying documentation were inspected, logged in and stored at recommended temperature. Drugs were freshly prepared just before each administration. No stock solution was prepared. Solutions were prepared in physiological saline. All solutions were administered in a volume of 100 µl for 20 g of weight.

Amyloid-β Peptides

Aβ$_{25-35}$

Denomination: amyloid-β protein (25-35), human, mouse, rat
CAS: 131602-53-4
Supplier: Polypeptides (France)
Reference: SC489
Batch: AW13285A
Molecular Weight: 1060.28
Storage Temp: −20° C.
Appearance: white powder Sc.Aβ:

Denomination: scrambled amyloid-β protein (25-35), human, mouse, rat
CAS: NA
Supplier: Polypeptides (France)
Reference: SC942
Batch: AW13157A
Molecular Weight: 1060.26
Storage Temp: −20° C.
Appearance: white powder The homogeneous oligomeric preparation of Aβ$_{25-35}$ peptide was performed according to the AMYLGEN's own procedure. Each mouse was anesthetized with isoflurane 2.5% and injected i.c.v. with Aβ$_{25-35}$ peptide (9 nmol/mouse) or Sc.Aβ peptide (9 nmol/mouse), in a final volume of 3 µl/mouse, according to the previously described method (Maurice T, et al. (1996). *Brain Res.* 706(2): 181-193, Maurice T, et al. (1998) *Neuroscience* 83(2): 413-428, Meunier J, et al. (2006) *British J. Pharmacol.* 149(8): 998-1012, Villard V, et al. (2009) *Neuropsychopharmacology* 34(6): 1552-1566, Villard V, et al. (2011) *J. Pharmacol. Sci.* 115(3): 279-292).

Animals: Male Swiss mice, 6 weeks old and weighing 30-35 g, from JANVIER (Saint Berthevin, France), were kept for housing and experiments took place within the animal facility building of the University of Montpellier 2 (CECEMA, Office of Veterinary Services agreement #B-34-172-23). Animals were housed in groups with access to food and water ad libitum, except during behavioral experiments. They were kept in a temperature and humidity controlled animal facility on a 12 h/12 h light/dark cycle (lights off at 07:00 pm). Mice were numbered by marking their tail using permanent markers. All animal procedures were conducted in strict adherence to the European Union directive of Sep. 22, 2010 (2010/63/UE). Diagnostic summary reports of JANVIER were annexed to the study report.

Randomization of the animals: In each cage (n=8-10), each animal received a different treatment regimen. Animal surgery was performed on day 0 in a random manner by an experimenter not involved in the behavioral and biochemical experiments. The animals were coded as follows: experimenter code+cage number (letter)+mouse number in cage.

Mortality: Acute or delayed mortality was checked every day. No mouse died during the study.

Sacrifice: At the end of the passive avoidance retention session, on day 9, the animals were sacrificed by decapitation. The hippocampi and frontal cortex were dissected out and kept at −80° C. until the measurement of lipid peroxidation and other markers.

Spontaneous alternation performance: Immediate working memory performance was assessed by recording spontaneous alternation behavior during a single session in a Y-maze as described previously (Itoh J, et al. (1993) *Eur J Pharmacol* 236(3): 341-345; Hiramatsu M and Inoue K (1999) *Br J Pharmacol* 127(3): 655-660). The Y-maze is made of grey polyvinylchloride. Each arm of the Y-maze was 40 cm long, 3 cm wide, and 13 cm high at the bottom, 10 cm wide at the top, and converging at an equal angle. Each mouse was placed at the end of one arm and allowed to move freely through the maze during an 8 min session. The series of arm entries, including possible returns into the same arm, was checked visually. An alternation was defined as entries into all three arms on consecutive occasions. The number of maximum alternations is therefore the total number of arm entries minus two and the percentage of alternation was calculated as (actual alternations/maximum alternations)×100. Parameters included the percentage of alternation (memory index) and total number of arm entries (exploration index). Animals that showed an extreme behavior (Alternation percentage<20% or >90% or number of arm entries <10 were discarded from the calculation.

Passive avoidance test: The passive avoidance task was used to evaluate learning and memory in mice treated with igmesine. The apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshock (0.3 mA for 3 s) was delivered to the grid floor using a shock generator scrambler (Lafayette Instruments, Lafayette, USA). The guillotine door was initially closed during the training session. During training session, each mouse was placed into the white compartment. After 5 s, the door was raised. When the mouse entered the dark compartment and placed all its paws on the grid floor, the door was closed and the footshock delivered for 3 s. The step-through latency, that is, the latency spent to enter the dark compartment, and the number of vocalizations was recorded. The retention test was carried out 24 h after training. Each mouse was placed again into the white compartment. After 5 s, the door was raised. The step-through and escape latencies (corresponding to the re-exit from the dark compartment) were recorded up to 300 s. (Meunier J, et al. (2006). *British J. Pharmacol.* 149(8):

998-1012, Villard V, et al. (2009). *Neuropsychopharmacology* 34(6): 1552-1566, Villard V, et al. (2011). *J. Psychopharmacology* 25(8): 1101-1117). The animals that showed latencies lower than 10 s during the training and retention sessions were considered as failing to respond to the procedure and were discarded from the calculations.

Lipid peroxidation measurement: At day 24, 6 hippocampi from each group were used. After thawing, homogenates were homogenized in cold methanol (1/10 w/v), centrifuged at 1,000 g during 5 min and the supernatant placed in Eppendorf tube. The reaction volume of each homogenate was added to $FeSO_4$ 1 mM, $H_2SO_4$ 0.25 M, xylenol orange 1 mM and incubated for 30 min at room temperature. After reading the absorbance at 580 nm ($A_{580}1$), 10 µl of cumene hydroperoxyde (CHP) 1 mM was added to the sample and incubated for 30 min at room temperature, to determine the maximal oxidation level. The absorbance was measured at 580 nm ($A_{580}2$). The level of lipid peroxidation was determined as CHP equivalents according to: $CHPE = A_{580}1/A_{580}2 \times [CHP (nmol)]$ and expressed as CHP equivalents per wet weight of tissue and as percentage of control group data (Veh-treated Sc.Aβ-administered mice).

Enzyme-linked immunosorbant assay (ELISA) assays: Contents in GFAP, Caspase 12, Amyloid-beta 1-40, Amyloid-beta 1-42, Total Tau, and pTau on Ser199 were analyzed by using commercial ELISA assay kit.

GFAP: Supplier: USCNK #Ref: SEA068Mu
Total Tau: Supplier: Novex #Ref: KMB7011
pTau (S199): Supplier: Novex #Ref: KMB7041
Amyloid beta 1-40: Supplier: Novex #Ref: KMB3481
Amyloid beta 1-42: Supplier: Novex #Ref: KMB3441
Caspase-12: Supplier: LSBio #Ref: LS-F11023
BAX: Supplier: Euromedex #Ref: SEB343Mu
BCL2: Supplier: Euromedex #Ref: SEA778Mu For all assays, the cortices were homogenized after thawing in 50 mM Tris-150 mM NaCl buffer, pH 7.5, and sonicated for 20 s. After centrifugation (16,100 g for 15 min, 4° C.), The supernatants were collected and further used for ELISA assays according to the manufacturer instructions. For each assay, absorbance was read at 450 nm and sample concentration was calculated using a standard curve. Results were expressed in pg or ng of the protein marker per mg of tissue. The cortices from six mice per experimental group (n=36/ELISA kit) were assayed in duplicate.

Statistical analyses: Statistical analyses were performed on the different conditions using one-way ANOVA (F value), followed by the Dunnett's post-hoc multiple comparison test. All values, except passive avoidance latencies, were expressed as mean±S.E.M. Passive avoidance latencies do not follow a Gaussian distribution, since upper cut-off times are set. They were therefore analyzed using a Kruskal-Wallis non-parametric ANOVA (H value), followed by a Dunn's multiple comparison test. $p<0.05$ was considered as statistically significant.

Experiment 1 (Pre-Treatment): Results

Spontaneous alternation in the Y-maze: The $A\beta_{25-35}$ treatment induced highly significant spontaneous alternation deficits as compared to Sc.Aβ/Veh-injected mice (FIG. 1A). The igmesine pre-treatment dose-dependently prevented the $A\beta_{25-35}$-induced deficits, with the two active doses being 0.3 and 1 mg/kg (FIG. 1A). No effect was noted on locomotion (FIG. 1B).

Passive avoidance test: The $A\beta_{25-35}$ treatment induced highly significant passive avoidance deficits as compared to Sc.Aβ/Veh-injected mice, both in terms of step-through latency (FIG. 2A) and escape latency (FIG. 2B) during the retention session.

Figure 2:
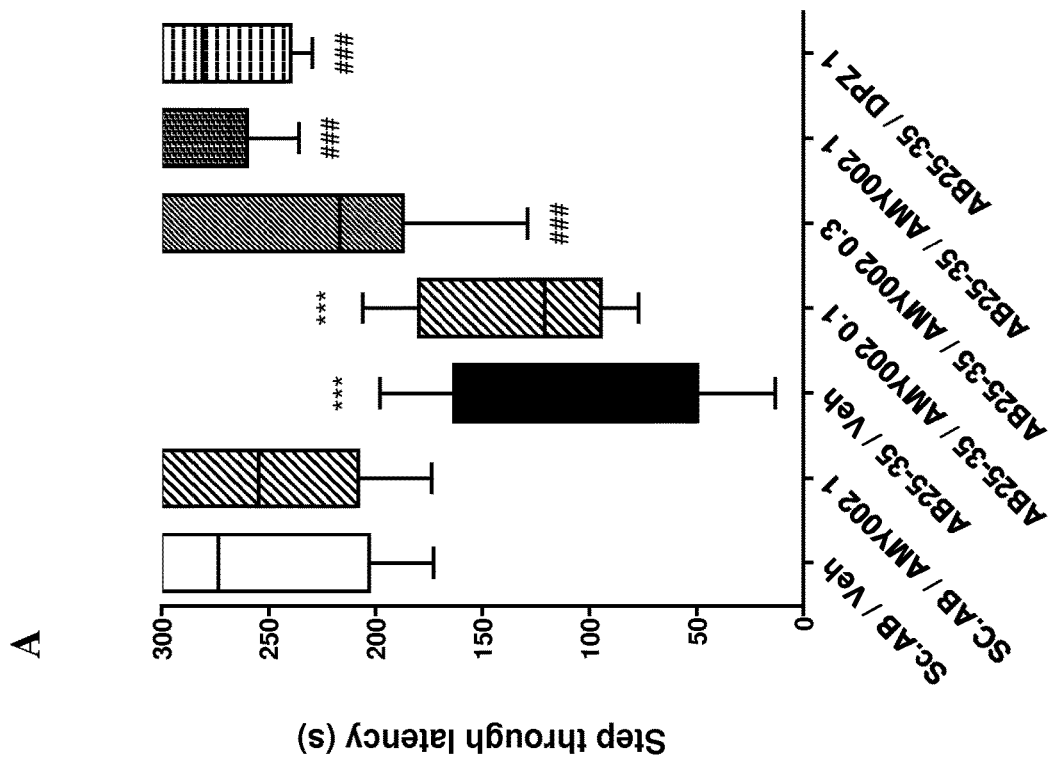
FIG. 2. Effects of igmesine (AMY002) on $A\beta_{25-35}$-induced passive avoidance in mice: (A) step-through latency and (B) escape latency were determined during the retention session. The mice were administered with igmesine i.p. 20 min before i.c.v. injection of $A\beta_{25-35}$ and the mice were tested to assess cognitive deficit at post-injection of igmesine or/DPZ. Veh, vehicle solution. *** $p<0.001$ vs. the Veh-treated Sc.Aβ group; ###$p<0.001$ vs. the $A\beta_{25-35}$ treated group; Dunnett's test. All doses expressed in mg/kg.

The igmesine pre-treatment dose-dependently prevented the $A\beta_{25-35}$-induced deficits, with a significant prevention at the two highest dose tested on the step-through latency parameter (FIG. 2A) and at the highest dose on escape latency (FIG. 2B).

Note that the treatments marginally affected the step-through latency and did not affect the shock sensitivity during the training session.

Figure 3:
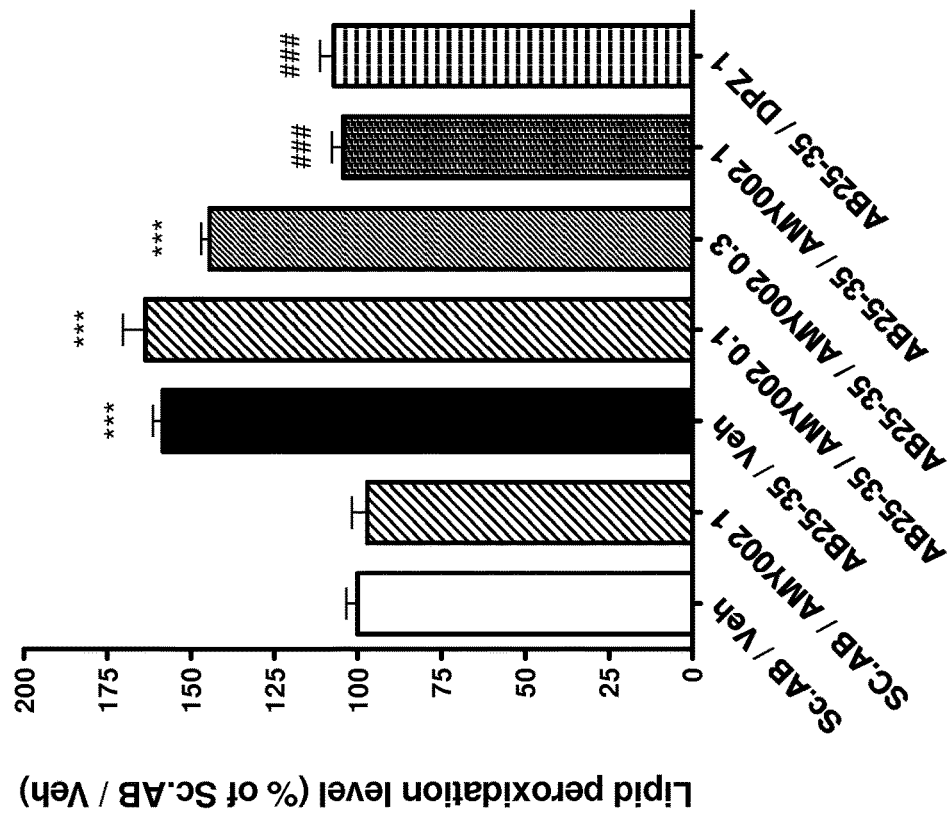
FIG. 3. Protective effect of igmesine (AMY002) on $A\beta_{25-35}$ induced elevation of hippocampal lipid peroxidation (LPO) levels as compared to donepezil (DPZ). Igmesine was injected IP 20 min before $A\beta_{25-35}$ injection. Veh, vehicle solution. *** $p<0.001$ vs. the Veh-treated Sc.Aβ group; ###$p<0.001$ vs. the Veh-treated $A\beta_{25-35}$ group; Dunnett's test. All doses expressed in mg/kg.

Lipid peroxidation: The $A\beta_{25-35}$ treatment induced highly significant increase of LPO as compared to Sc.Aβ/Veh-injected mice. The igmesine treatment fully normalized LPO levels at the dose of 1 mg/kg (FIG. 3).

Experiment 2 (6-Days Post-Treatment): Results

Figure 4:
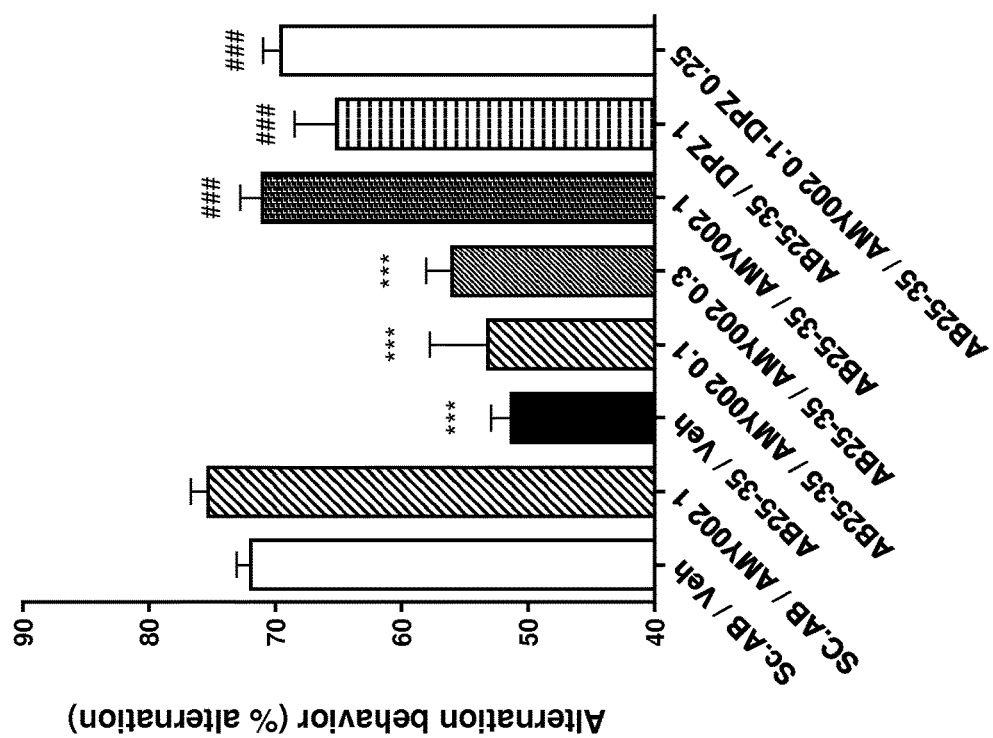
FIG. 4. Neuroprotective effect of igmesine (AMY002) on $A\beta_{25-35}$-induced spontaneous alternation deficits in mice 7 days after the injection of igmesine. Compared effect of donepezil (DPZ). Compounds were injected from day 1 after $A\beta_{25-35}$ injection until day 6. Veh, vehicle solution. *** $p<0.001$ vs. the V-treated Sc.Aβ group; ###$p<0.001$ vs. the Veh-treated $A\beta_{25-35}$ group; Dunnett's test. All doses expressed in mg/kg.

Spontaneous alternation in the Y-maze: The $A\beta_{25-35}$ treatment induced highly significant spontaneous alternation deficits as compared to Sc.Aβ/Veh-injected mice. The igmesine post-treatment prevented the $A\beta_{25-35}$-induced deficits at the highest doses tested (FIG. 4). No effect was noted on locomotion (results not shown).

Figure 5:
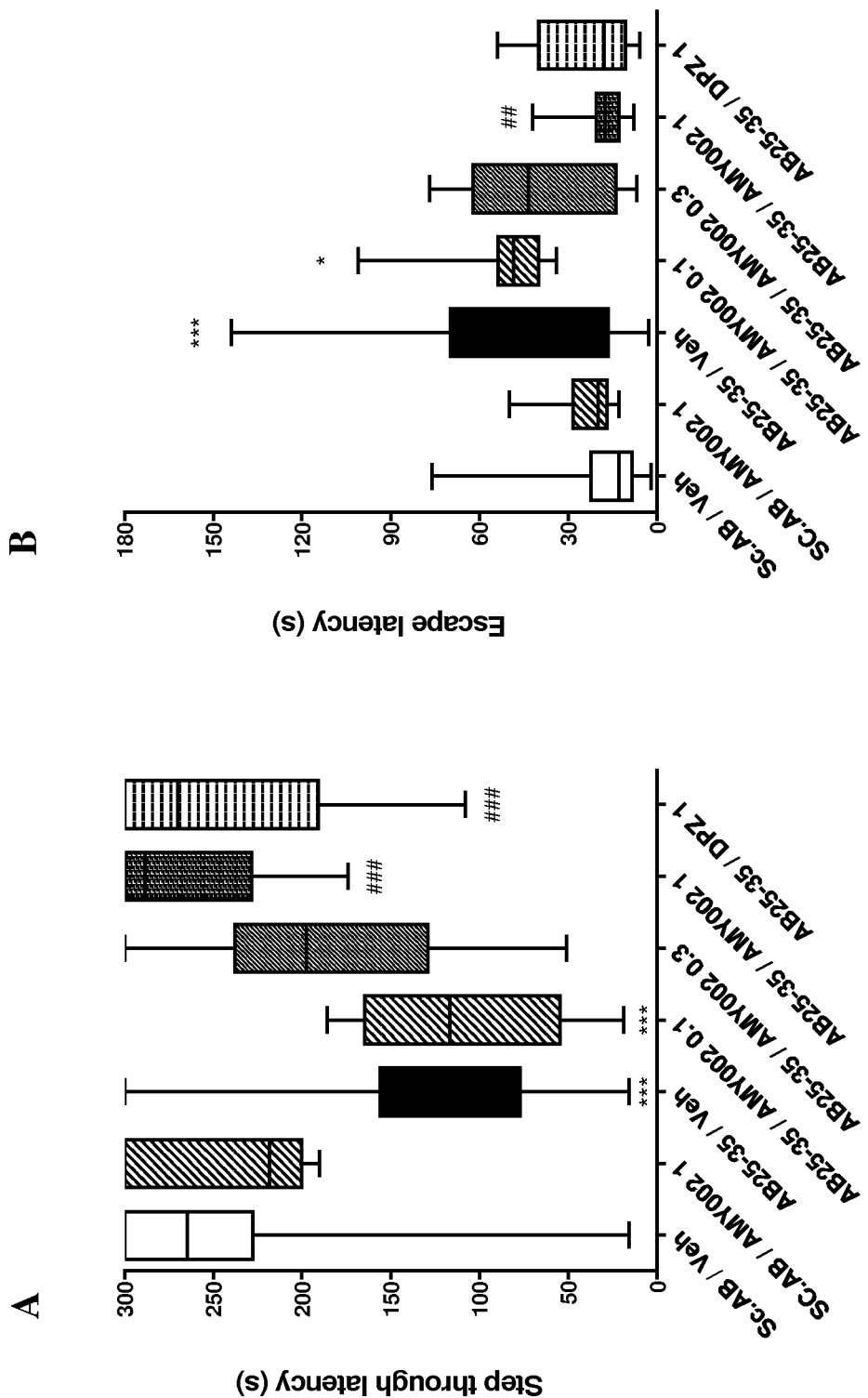
FIG. 5. Protective effects of igmesine (AMY002) or donepezil (DPZ) on $A\beta_{25-35}$-induced passive avoidance deficits in mice: (A) step-through latency was determined 8 days after the injection of the $A\beta_{25-35}$ peptide and (B) escape latency was measured during the retention session of 24 hours on day 9. Igmesine was injected from day 1 after $A\beta_{25-35}$ injection until day 6. Veh, vehicle solution. * $p<0.05$,  $p<0.01$, * $p<0.001$ vs. the V-treated Sc.Aβ group; ##$p<0.01$, ###$p<0.001$ vs. the $A\beta_{25-35}$-treated group; Dunnett's test. All doses expressed in mg/kg.

Passive avoidance test: The $A\beta_{25-35}$ treatment induced highly significant passive avoidance deficits as compared to Sc.Aβ/Veh-injected mice, both in terms of step-through latency (FIG. 5A) and escape latency (FIG. 5B) during the retention session. The igmesine post-treatment dose-dependently prevented the $A\beta_{25-35}$-induced deficits, with a significant prevention at the highest dose tested on the step-through latency parameter (FIG. 5A) and escape latency (FIG. 5B). Note that the treatments did not affect the step-through latency and the shock sensitivity during the training session.

Figure 6:
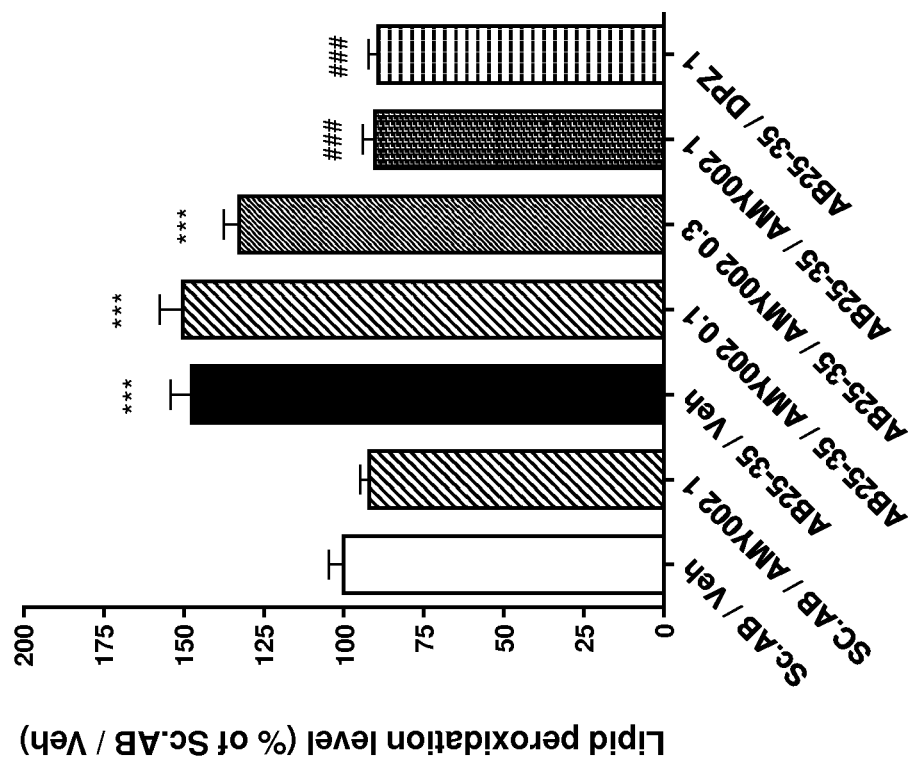
FIG. 6. Effect of igmesine (AMY002) or donepezil (DPZ) on $A\beta_{25-35}$-induced elevation of hippocampal LPO levels in mice. LPO levels were used as a marker of the oxidative stress. Igmesine was injected 24 hours after $A\beta_{25-35}$ injection and once daily up to day 6 and mouse brains were collected after the passive avoidance test on day 9. All results expressed as percent of Sc.Aβ (% of Sc.Aβ) group. Veh, vehicle solution. *** $p<0.001$ vs. the Veh-treated Sc.Aβ group; ###$p<0.001$ vs. the Veh-treated $A\beta_{25-35}$ group; Dunnett's test. All doses expressed in mg/kg.

Lipid peroxidation: The $A\beta_{25-35}$ treatment induced highly significant increase of LPO as compared to Sc.Aβ/Veh-injected mice. The igmesine treatment fully normalized LPO levels at the dose of 1 mg/kg (FIG. 6).

Figure 7:
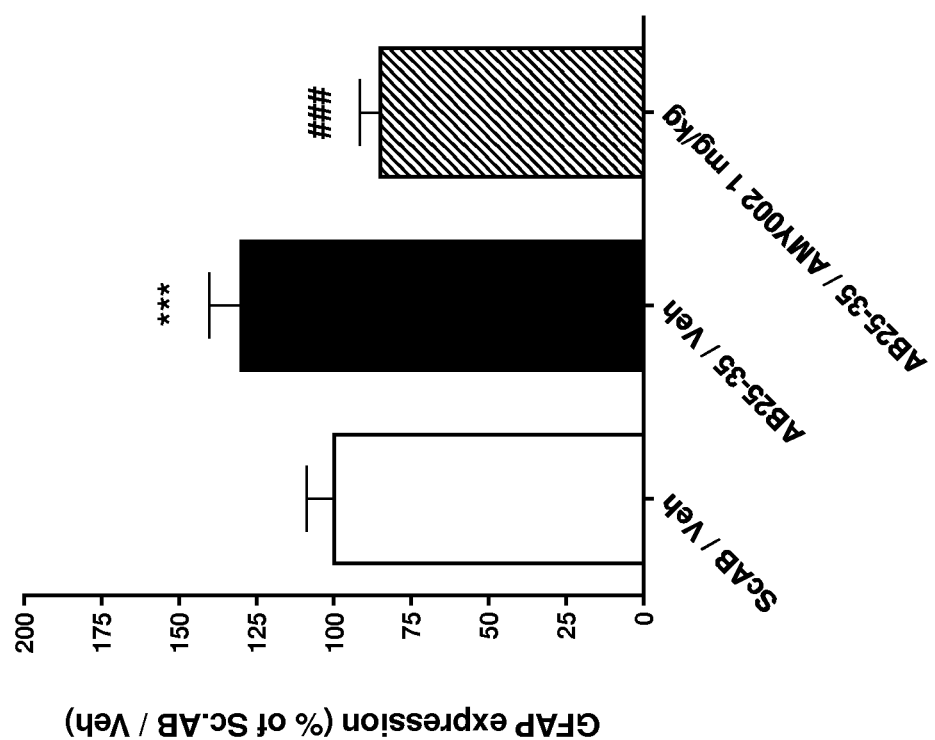
FIG. 7. Effect of igmesine (AMY002) on $A\beta_{25-35}$-induced elevation of cortical glial fibrillary acidic protein (GFAP) levels in mice. GFAP levels were used a marker as a neurologic damage. Igmesine was injected 24 hours after $A\beta_{25-35}$ injection up to day 6 and brains were collected after the passive avoidance test on day 9. All results expressed as percent of Sc.Aβ (% of Sc.Aβ) group. Veh, vehicle solution. *** $p<0.001$ vs. the Veh-treated Sc.Aβ group; ###$p<0.001$ vs. the Veh-treated $A\beta_{25-35}$ group; Dunnett's test.

GFAP: The $A\beta_{25-35}$ treatment induced a highly significant increase of GFAP, one of the best known hallmarks of reactive astrocytes. The igmesine treatment fully normalized GFAP elevation produced by $A\beta_{25-35}$ treatment at the dose of 1 mg/kg (FIG. 7).

Figure 8:
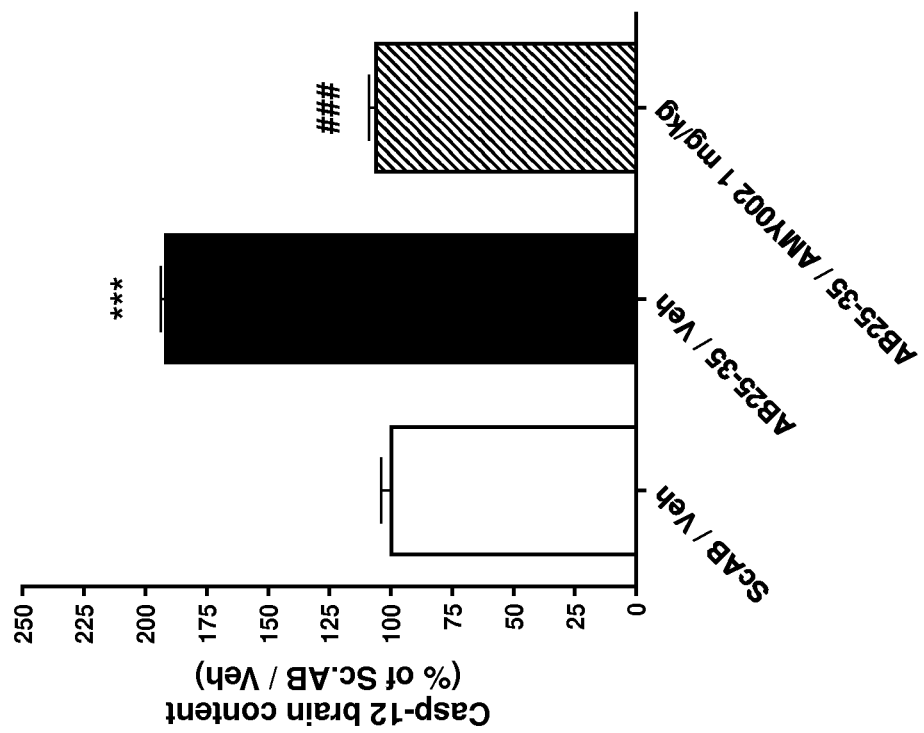
FIG. 8. Protective effect of igmesine (AMY002) on $A\beta_{25-35}$ induced elevation of cortical caspase 12 levels in mice. Caspase levels were used as a marker of ER stress. Igmesine was injected 24 hours after $A\beta_{25-35}$ injection up to day 6 and brains were collected after the passive avoidance test on day 9. All results expressed as percent of Sc.Aβ (% of Sc.Aβ) group. Veh, vehicle solution. * $p<0.001$ vs. the Veh-treated Sc.Aβ group; ###$p<0.001$ vs. the Veh-treated $A\beta_{25-35}$ group; Dunnett's test FIG. 9. Effect of igmesine (AMY002) on $A\beta_{25-35}$ induced elevation of $A\beta_{1-40}$ and $A\beta_{1-42}$ levels in the mouse cortex. Igmesine was injected 24 hours after $A\beta_{25-35}$ injection up to day 6 and brains were collected after the passive avoidance test on day 9. All results expressed as percent of Sc.Aβ (% of Sc.AB) group. Veh, vehicle solution. * $p<0.001$ vs. the Veh-treated Sc.Aβ group; ###$p<0.001$ vs. the Veh-treated $A\beta_{25-35}$ group; Dunnett's test FIG. 10. Protective effect of igmesine (AMY002) on $A\beta_{25-35}$ induced elevation of cortical Tau protein phosphorylated at Serine 199 (pTauS199). p-tau levels were used as a biomarker of Alzheimer's disease. Igmesine was injected 24 hours after $A\beta_{25-35}$ injection up to day 6 and brains were collected after the passive avoidance test on day 9. All results expressed as percent of Sc.Aβ (% of Sc.Aβ) group. Veh, vehicle solution. * $p<0.001$ vs. the Veh-treated Sc.Aβ group; ###$p<0.001$ vs. the Veh-treated $A\beta_{25-35}$ group; Dunnett's test FIG. 11. Effect of igmesine (AMY002, 1 mg/kg) on $A\beta_{25-35}$-induced elevation of cortical Bax/Bcl2 ratio. Bax/Bcl2 ratio was used as a marker of apoptosis associated with progress of the disease. Igmesine was injected 24 hours after $A\beta_{25-35}$ injection up to day 6 and brains were collected after the passive avoidance test on day 9. All results expressed as percent of Sc.Aβ (% of Sc.Aβ) group. Veh, vehicle solution. * $p<0.001$ vs. the Veh-treated Sc.Aβ group; ###$p<0.001$ vs. the Veh-treated $A\beta_{25-35}$ group; Dunnett's test.

Caspase 12: The $A\beta_{25-35}$ treatment induced highly significant increase of caspase 12, a marker of endoplasmic reticulum stress. The igmesine treatment fully normalized caspase 12 elevation at the dose of 1 mg/kg (FIG. 8).

Figure 9:
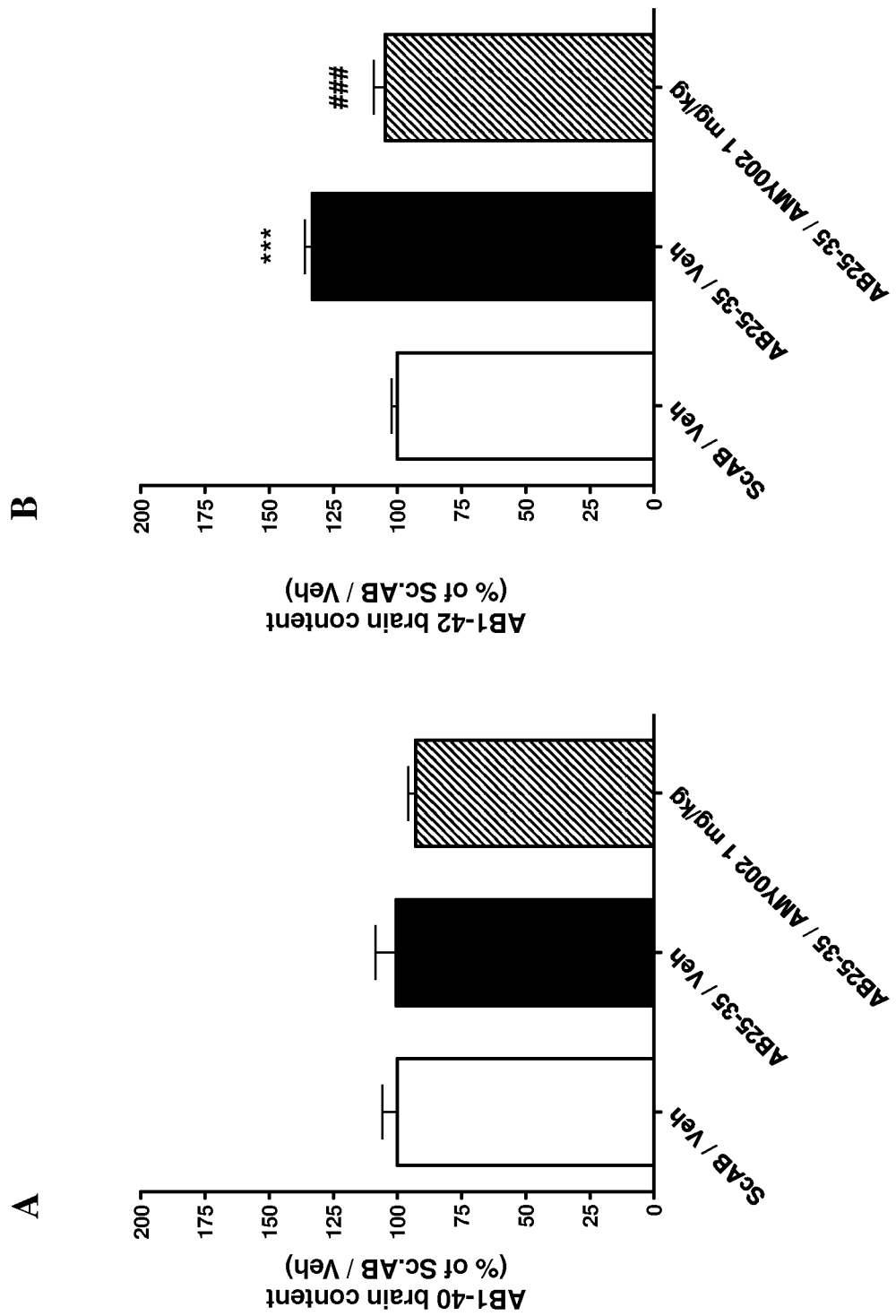

Amyloid beta processing: The $A\beta_{25-35}$ treatment induced highly significant increase of $A\beta_{1-42}$ but not of $A\beta_{1-40}$ cortical contents. The igmesine treatment fully normalized $A\beta_{1-42}$ elevation produced by $A\beta_{25-35}$ treatment (FIG. 9).

Figure 10:
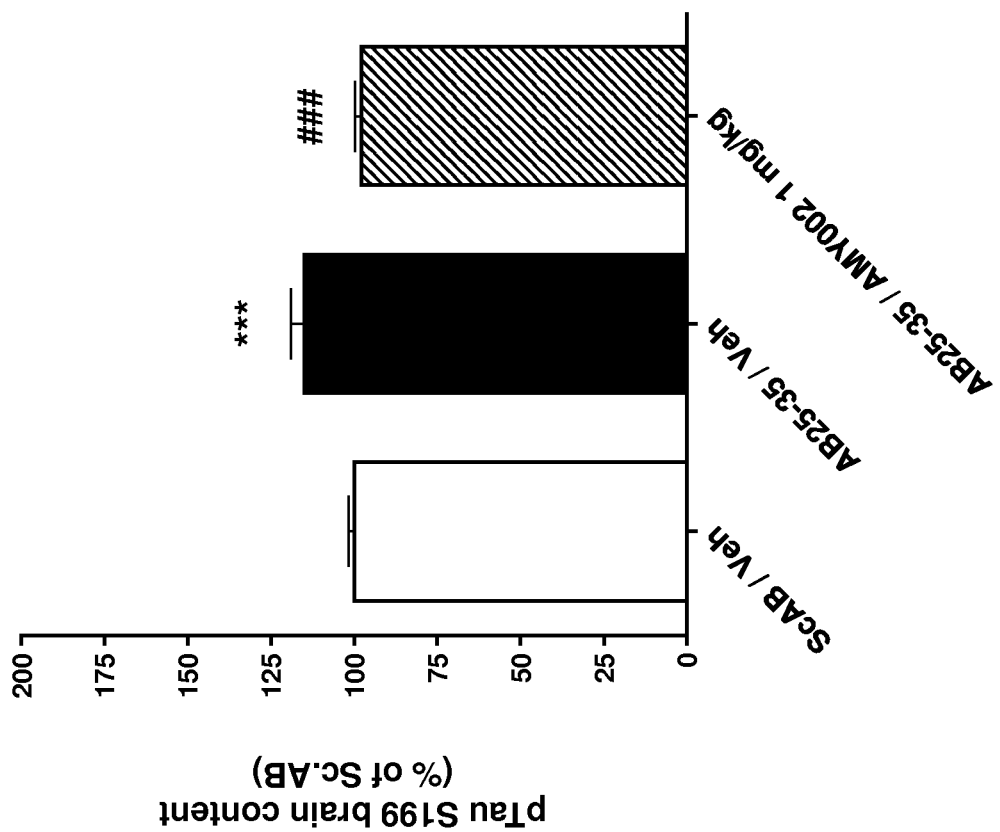

Tau processing: The $A\beta_{25-35}$ treatment induced highly significant increase of cortical Tau protein phosphorylated on Serine 199 (pTauS199) as compared to Sc.Aβ/Veh-injected mice. The igmesine treatment fully normalized the elevation of Tau protein phosphorylated on Serine 199 (pTauS199) produced by $A\beta_{25-35}$ treatment (FIG. 10).

Figure 11:
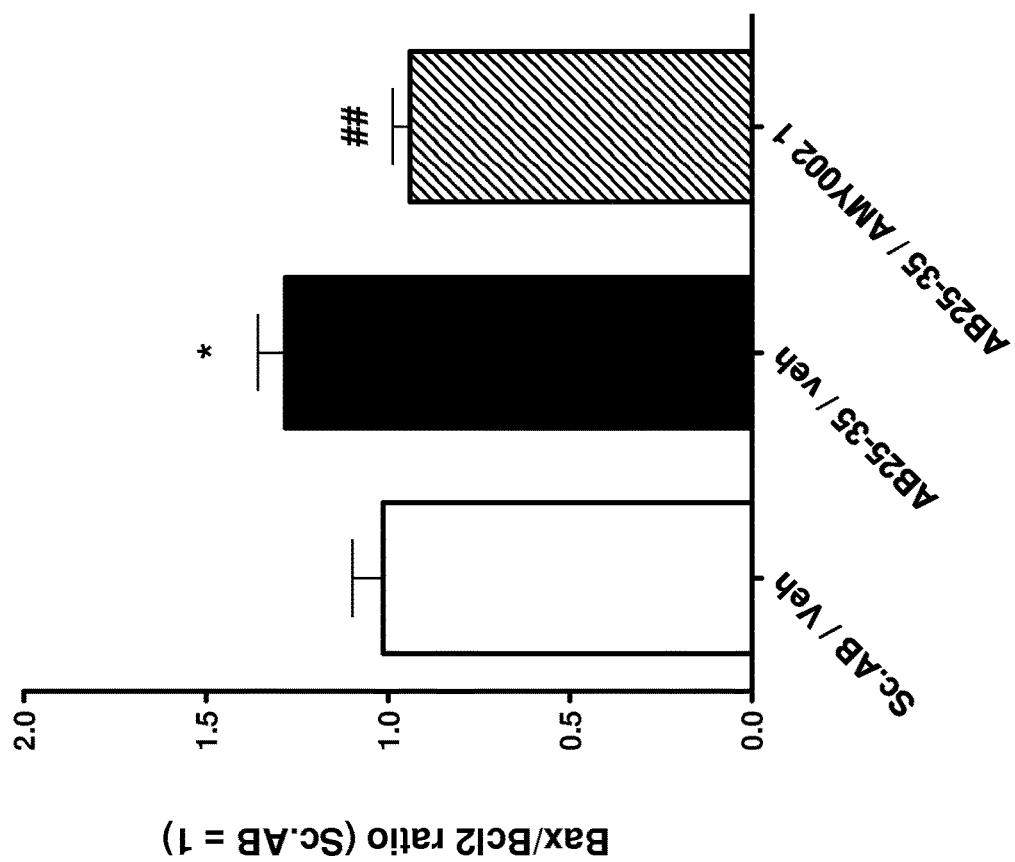

Apoptosis: The $A\beta_{25-35}$ treatment induced highly significant cortical increase of Bax/Bcl-2 as compared to Sc.Aβ/Veh-injected mice. The Bcl-2 proteins are a family of evolutionarily related proteins mainly involved in regulating programmed cell death (apoptosis). Bax is the most studied member of the family and has pro-apoptotic activity, while Bcl-2 itself is the most investigated family member with anti-apoptotic activity. AM002 treatment fully normalized Bax/Bcl-2 ratio elevation. (FIG. 11).

Experiment 3 (Combination Study with Donepezil and Memantine): Results

Figure 12:
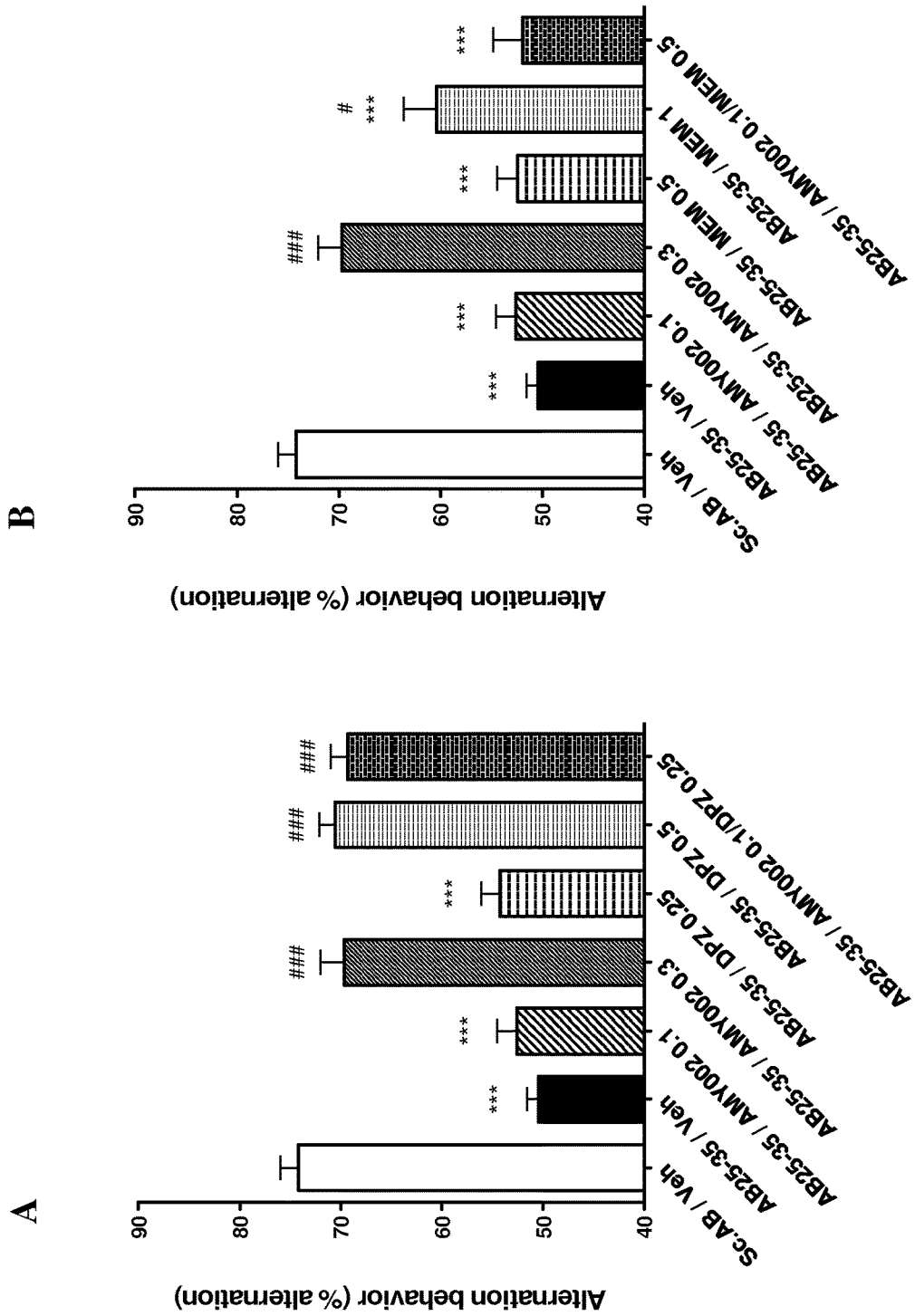
FIG. 12. Effect of igmesine (AMY002) in combination with the sigma-1R agonists donepezil (DPZ) (A) or with memantine (MEM) (B) on $A\beta_{25-35}$-induced spontaneous alternation deficits in mice. Veh, vehicle solution. *** $p<0.001$ vs. the Veh-treated Sc.Aβ group; #$p<0.05$, ###$p<0.001$ vs. the Veh-treated $A\beta_{25-35}$ group; Dunnett's test. All doses expressed in mg/kg.

Spontaneous alternation in the Y-maze: The $A\beta_{25-35}$ treatment induced highly significant spontaneous alternation deficits as compared to Sc.Aβ/Veh-injected mice (FIG. 12).

The two doses tested for each compound allowed to determine the highest sub-active dose: 0.1 mg/kg for igmesine, 0.25 mg/kg for donepezil and 0.5 mg/kg for memantine. The combinations based on these doses were then tested. The (igmesine+donepezil) mix led to a highly significant protection. The (igmesine+memantine) mix did not.

Figure 13:
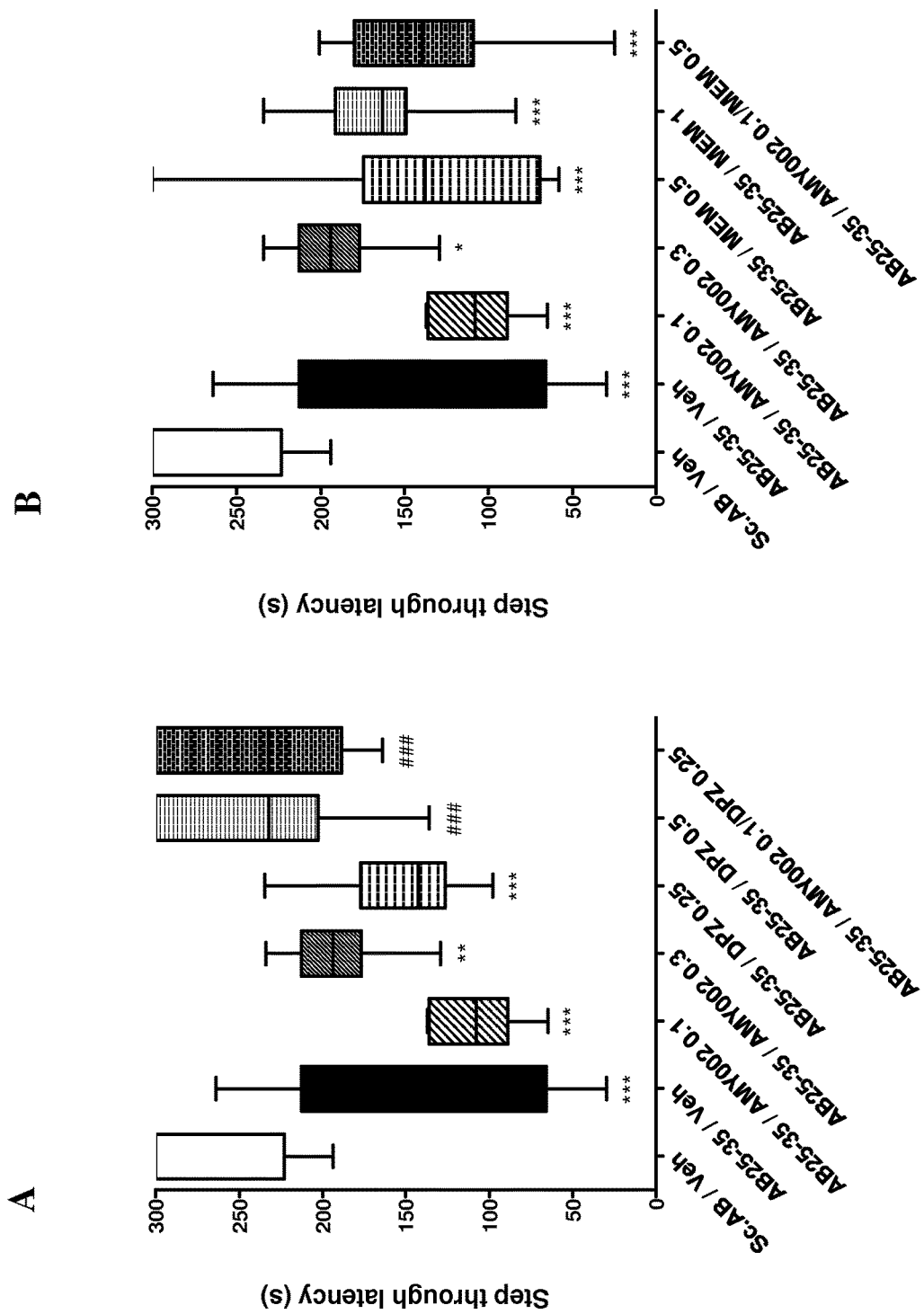
FIG. 13. Effect of igmesine (AMY002) in combination with the sigma-1R agonists donepezil (DPZ) (A) or with memantine (MEM) (B) on $A\beta_{25-35}$-induced passive avoidance deficits in mice. Passive avoidance test was to assess short-term or long-term memory on mice. Veh, vehicle solution. * $p<0.05$,  $p<0.01$, * $p<0.001$ vs. the Veh-treated Sc.Aβ group; ###$p<0.001$ vs. the $A\beta_{25-35}$-treated group; Dunnett's test. All doses expressed in mg/kg.

Passive avoidance test: The $A\beta_{25-35}$ treatment induced highly significant passive avoidance deficits as compared to Sc.Aβ/Veh-injected mice in terms of step-through latency (FIG. 13) during the retention session. The two doses tested for each compound allowed the determination of the sub-active doses for igmesine and memantine. The (igmesine+donepezil) mix led to a highly significant protection. The (igmesine+memantine) mix did not.

Figure 14:
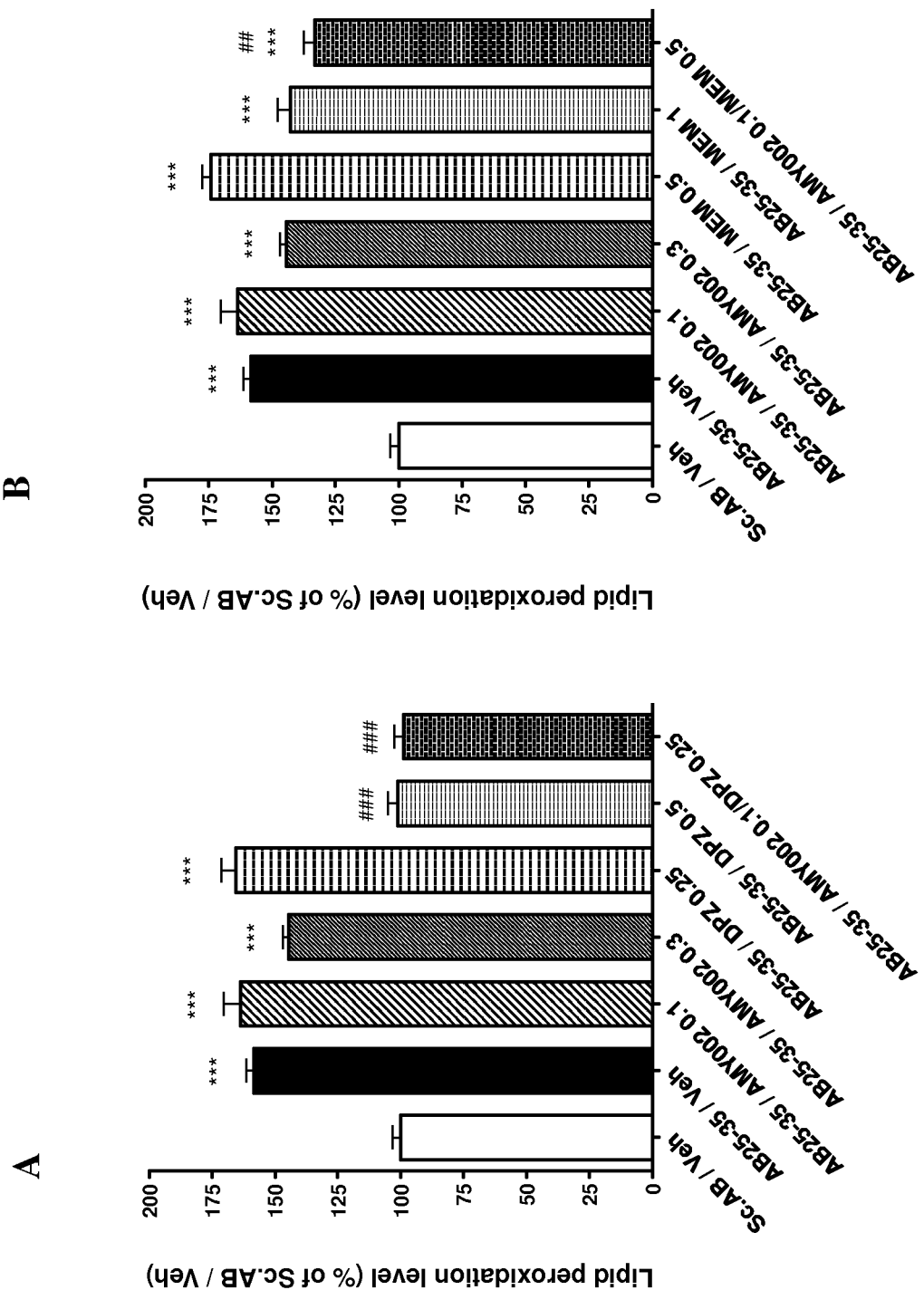
FIG. 14. Effect of igmesine (AMY002) in combination with the sigma-1R agonists donepezil (A) or memantine (B) on $A\beta_{25-35}$ induced elevation of hippocampal LPO levels. Igmesine and donepezil were injected i.p. 20 min before $A\beta_{25-35}$ injection. Veh, vehicle solution. *** $p<0.001$ vs. the Veh-treated Sc.Aβ group; ##$p<0.01$, ###$p<0.001$ vs. the Veh-treated $A\beta_{25-35}$ group; Dunnett's test. All doses expressed in mg/kg.

Lipid peroxidation: The $A\beta_{25-35}$ treatment induced highly significant increase of LPO as compared to Sc.Aβ/Veh-injected mice. The igmesine treatment at a subactive dose of 0.1 mg/kg did synergize with the subactive dose of donepezil (0.25 mg/kg) while such a synergy was not present with memantine (FIG. 14).

Figure 15:
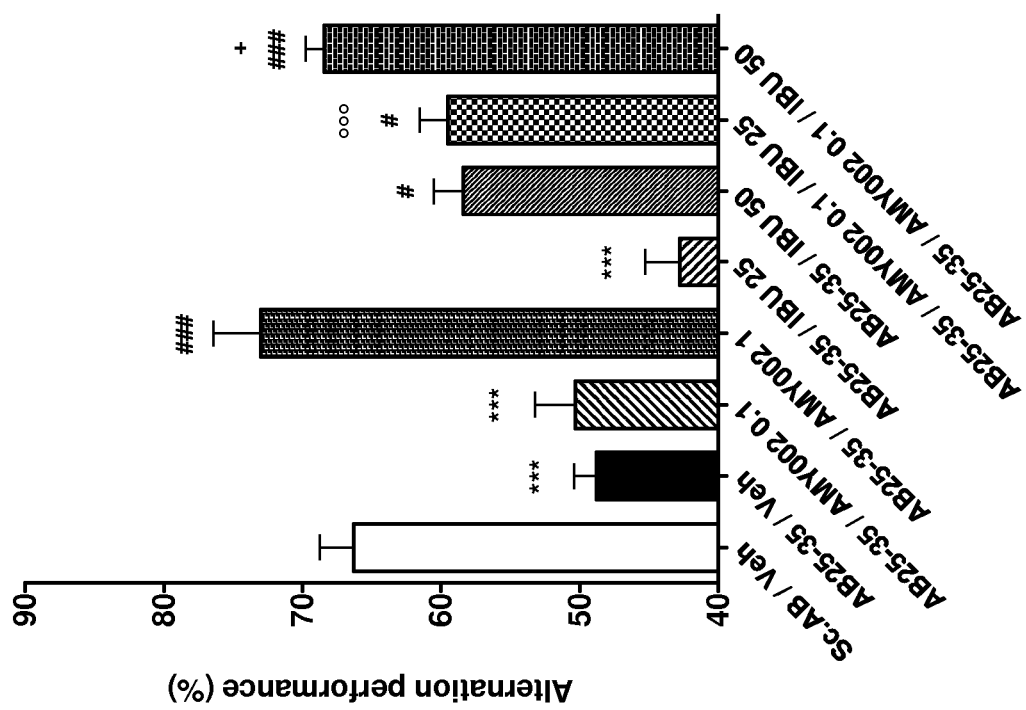
FIG. 15. Protective effect of igmesine (AMY002) in combination with ibuprofen (IBU) on $A\beta_{25-35}$ induced spontaneous alternation deficits in mice. Igmesine and ibuprofen were injected IP 24 hours after $A\beta_{25-35}$ injection up to day 6 and brains were collected after the passive avoidance test on day 9. Veh, vehicle solution. *** p<0.001 vs. the Veh-treated Sc.Aβ group; #p<0.05 ###p<0.001 vs. the Veh-treated Aβ$_{25-35}$ group; +p<0.05 vs. the IBU 50 treated Aβ$_{25-35}$ group; ○○○ p<0.001 vs. the IBU 25 treated Aβ$_{25-35}$ group; Dunnett's test._All doses expressed in mg/kg.
Figure 16:
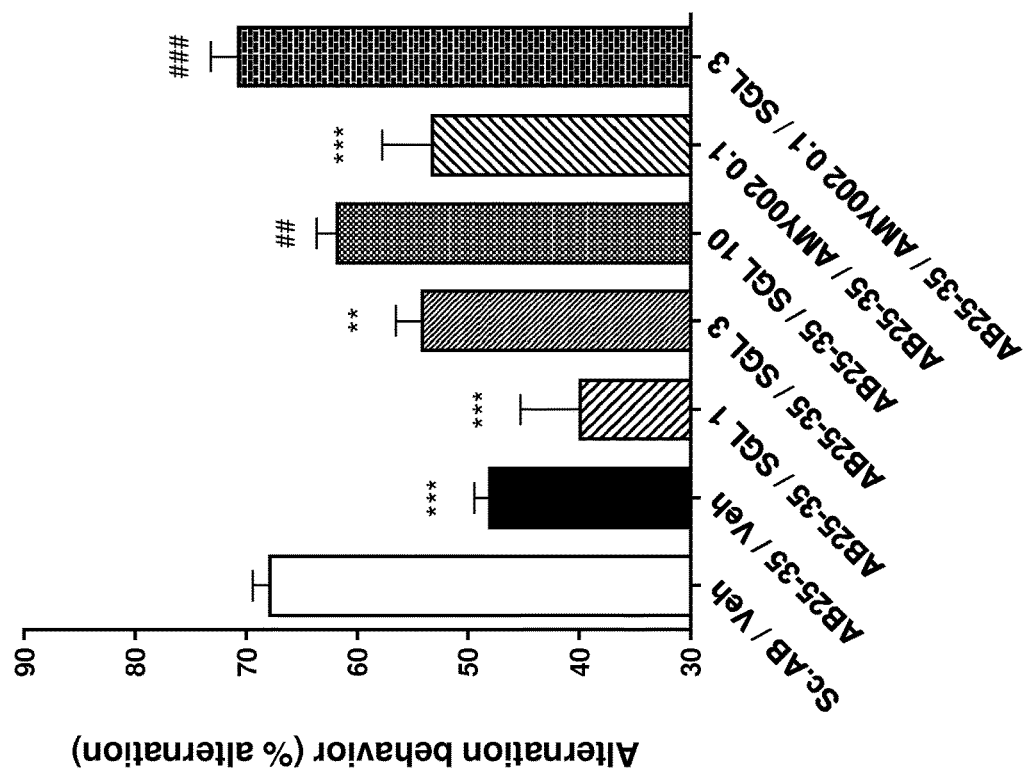
FIG. 16. Protective effect of igmesine (AMY002) in combination with selegiline (SGL) on Aβ$_{25-35}$ induced spontaneous alternation deficits in mice. Igmesine and ibuprofen were injected IP 24 hours after Aβ$_{25-35}$ injection up to day 6 and brains were collected after the passive avoidance test on day 9. V, vehicle solution. p<0.01, *p<0.001 vs. the Veh-treated Sc.Aβ group; ##p<0.01 ###p<0.001 vs. the Veh-treated Aβ$_{25-35}$ group; Dunnett's test. All doses expressed in mg/kg.
Figure 17:
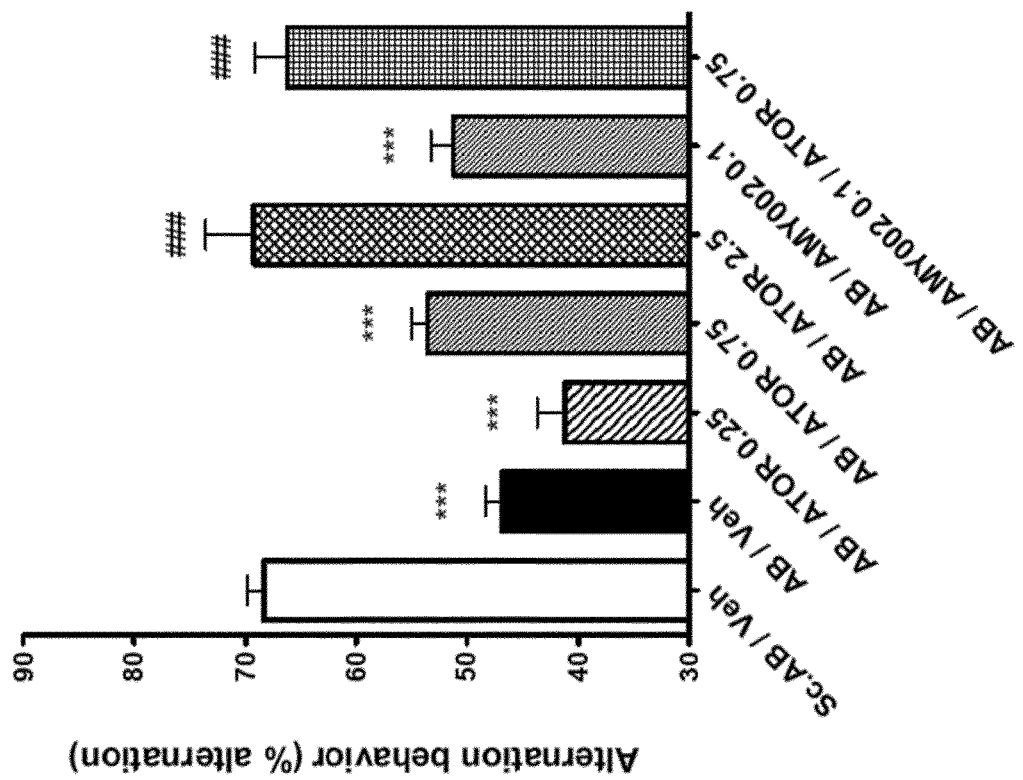
FIG. 17. Protective effect of igmesine (AMY002) in combination with a cholesterol lowering medication atorvastatin (ATOR) on Aβ$_{25-35}$ (AB)-induced spontaneous alternation deficits in mice. Igmesine and atorvastatin were injected IP 24 hours after Aβ$_{25-35}$ injection up to day 6 and brains were collected after the passive avoidance test on day 9. V, vehicle solution. *** p<0.001 vs. the V-treated Sc.Aβ group; ###p<0.001 vs. the V-treated Aβ$_{25-35}$ group; Dunnett's test.

Experiment 4 (Combination Study with Ibuprofen, Selegiline and Atorvastatin): Results Ibuprofen, selegiline and atorvastatin where able to protect mice from injury produced by $A\beta_{25-35}$ treatment in a dose dependent manner. When sub-active doses of the three compounds were selected to be associated to igmesine at 0.1 mg/kg, inactive by itself, we observed a very significant reversion of the memory deficits as shown in FIG. 15, FIG. 16 and FIG. 17.

Discussion

The present data demonstrate that, using an acute model of Alzheimer's disease toxicity, igmesine is neuroprotective. The drug prevented the appearance of learning and memory deficits in two procedures assessing different types of memory processes: spatial working memory for the Y-maze test and contextual long-term memory for the passive avoidance test. Both the pre-treatment and post-treatment showed a significant efficacy. This protectant effect observed on memory capacities was correlated to a similar protectant effect on two effects of oxidative stress we could measure: lipid peroxidation (LPO levels) and ER stress (caspase 12). Further analysis showed that igmesine treatment was able to regulate neuroinflammation activation as demonstrated by the decrease of GFAP, a marker of astrocyte activation, as well as apoptosis activation by using the elevation of the ratio Bax/Bcl2 as a marker. Two important markers of the pathology were also normalized in our model: $A\beta_{1-42}$ elevation and pTauS199.

The effect of igmesine was observed at doses as low as 0.3 mg/kg, when given as a preventive treatment, or 1 mg/kg as a curative treatment (starting 1 day after induction of the toxicity) to be compared to the antidepressant effects which have been reported to happen at doses higher than 30 mg/kg. The efficacy of igmesine was determined to be 30 to 100-fold higher on neuroprotection in mouse models of Alzheimers disease (AD) than that in mouse models of depression. Moreover, when used in combination with donepezil, ibuprofen, selegiline or atorvastatin, the drug showed a clear synergistic effect that was not observed with memantine. This combinations allowed to use igmesine at a dose 300-fold lower than the dose active on depression. The dose of donepezil could be lowered by 4-fold when associated to igmesine.

Similarly, co-administration of ibuprofen or atorvastatin with very low dose igmesine resulted in total neuroprotection at doses 3-fold or 10-fold lower, respectively, than the doses usually prescribed for ibuprofen or atorvastatin in humans (calculated from values obtained after allometric scaling calculation from mouse to human). Selegiline displayed protective effects at the same doses used for the treatment of depression in humans. Besides its own neuroprotective effects, igmesine at low doses opens new avenues for the treatment of AD by widening the safety window of other potential therapeutic tools.

Example 2

Effect of Igmesine in a Model of Parkinson's Disease: 6OHDA Injury in Rat Primary Dopaminergic Neurons sRat Primary Cultures of Dopaminergic Neurons Rat dopaminergic neurons were cultured as described (Schinelli S, et al. *Journal of neurochemistry* 50(6): 1900-1907). Briefly pregnant female rats of 15 days gestation were killed by cervical dislocation (Rats Wistar; Janvier) and the foetuses removed from the uterus. The embryonic midbrains were removed and placed in ice-cold medium of Leibovitz 15 (L15; PanBiotech, Ref P04-27055, Batch: 8810315) containing 2% of Penicillin-Streptomycin (PS; PanBiotech, ref: P06-07100, Batch: 7511015) and 1% of bovine serum albumin (BSA; PanBiotech, Ref: P06-1391100, Batch: H140904). Only the ventral portions of the mesencephalic flexure were used for the cell preparations as this region of the developing brain is rich in dopaminergic neurons. The midbrains were dissociated by trypsinization for 20 minutes (min) at 37° C. (Trypsin EDTA 1x; PanBiotech, Ref: P10-023100, batch: 1670415). The reaction was stopped by the addition of Dulbecco's modified Eagle's medium (DMEM; PanBiotech, Ref: P04-03600, Batch: 9021115) containing DNase I grade II (0.1 mg/ml; PanBiotech, Ref: P60-37780100, Batch: H140508) and 10% of fetal calf serum (FCS; Invitrogen). Cells were then mechanically dissociated by 3 passages through a 10 ml pipette. Cells were then centrifuged at 180×g for 10 min at 4° C. on a layer of BSA (3.5%) in L15 medium. The supernatant was discarded and the cell pellets were re-suspended in a defined culture medium consisting of Neurobasal (Invitrogen, Ref: 21103, Batch: 1754639) supplemented with B27 (2%; Invitrogen, ref: 17504, batch: 1799273), L-glutamine (2 mM; PanBiotech, Ref: P04-80100, Batch: 6620314) and 2% of PS, 10 ng/mL of BDNF (PanBiotech, Ref: CB-1115002, Batch: 121027) and 1 ng/mL of GDNF (PanBiotech, Ref: CB-1116001, Batch: H151004). Viable cells were counted in a Neubauer cytometer using the trypan blue exclusion test. The cells were seeded at a density of $4 \times 10^4$ cells/well in 96 well-plates (pre-coated with poly-D-lysine; Greiner, Ref: E150033VJ) and were cultured at 37° C. in a humidified air (95%)/$CO_2$ (5%) atmosphere. Half of the medium was changed every 2 days with fresh medium. In these conditions, after 5 days of culture, astrocytes are present in the culture and release growth factor allowing neurons differentiation. Five to six percent of the neuronal cell population was dopaminergic neurons.

Neuroprotective Effect of Igmesine on Rat Dopaminergic Neurons

Briefly, on day 6 of culture, cells were pre-treated for 1 h with test compound or reference compound then intoxicated with 6OHDA (20 µM) for 48 h. The following conditions were done:
☐_Control (DMSO 0.1%)
☐_+6OHDA (20 µM, 48 h)/DMSO 0.1%
☐_+6OHDA (20 µM, 48 h+BDNF (50 ng/ml) as a reference compound
☐_+6OHDA (20 µM, 48 h)+Igmesine (0.1 µM, 0.3 µM, 1 µM, 3 µM, 10 µM, 30 µM, 100 µM)
One culture was done with 6 wells per condition.
End Point Evaluation: Measure of Total Number of Rat Dopaminergic Neurons After 48 hours of intoxication in presence or absence of test compound, cells were fixed by a solution of 4% paraformaldehyde (Sigma, ref 6148, batch: SLBH4356V) for 20 min at room temperature, the control conditions was fixed as well following the same procedure. The cells were then permeabilized and non-specific sites were blocked with a solution of phosphate buffered saline (PBS; PanBiotech; ref: P04-36500, Batch: 7250616) containing 0.1% of saponin (Sigma; ref: S7900, Batch: BCBJ8417V) and 1% fetal calf serum (FCS) for 15 min at room temperature. Cells were incubated with Monoclonal Anti-Tyrosine Hydroxylase antibody produced in mouse (TH, antibodies-Sigma; ref: T1299, Batch: 101M4796) PBS containing 1% FCS, 0.1% saponin, for 2 h at room temperature. Antibody against TH stained dopaminergic neuron.

The antibody was revealed with Alexa Fluor 488 goat anti-mouse IgG (Molecular probe, ref: A11001, Batch: 1752514) in PBS with 1% FCS, 0.1% saponin, for 1 h at room temperature. Nuclei of cells were labelled by a fluorescent marker (Hoechst solution, Sigma; ref: B1155, Batch: 011M4004V) in the same solution.

Figure 18:
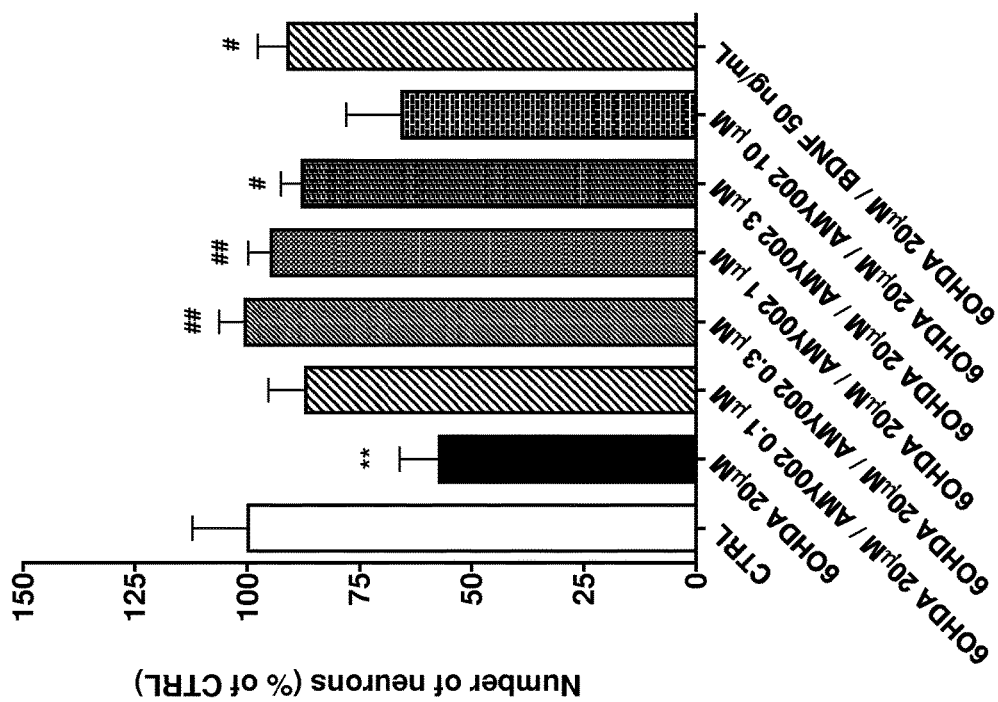
FIG. 18. Effect of igmesine (AMY002) on the survival of murine primary dopaminergic neurons culture injured by a neurotoxic synthetic compound 6-hydroxydopamine or 2,4,5-trihydroxyphenethylamine (6-OHDA, 20 ∞M, 48 h). The number of live neurons was expressed in percentage of untreated control (% of CTRL). (mean±s.e.m; **p<0.01 6OHDA vs control; #p<0.05; ##p<0.01 igmesine or BDNF vs. 6OHDA group; one way ANOVA followed by Dunnett's test. TH positive neurons number (labelled with a secondary antibody coupled to Alexa 488) was significantly reduced by the application of 6OHDA.

For each condition, 20 pictures per well were taken using InCell Analyzer™ 2000 (GE Healthcare) with 20× magnification. Images of each culture well were taken in same condition. Analysis of cell bodies of TH positive neurons was performed using Developer software (GE healthcare). A total of 6 data per experimental condition were provided
Statistics The data were expressed as mean±s.e.m. (of 6 data per condition, 1 culture). The data were analyzed using a one-way analysis of variance (ANOVA) following by Dunnett's test and p<0.05 was considered statiscally significant.
Results According to FIG. 18, 6OHDA applied at 20 µM for 48 h induced a large and significant decrease of TH positive neurons (**, p<0.01, 57.14% of the control). Application of BDNF (50 ng/mL) displays a protective effect against 6OHDA injury (#p<0.05, 91.03% of the control). This result validates the study. Igmesine (AMY002) at 0.3 µM, 1 µM (##p<0.01, 94.58% and 100.49% of the control, respectively) and 3 µM (#p<0.05, 87.68% of the control), shows a significant protective effect against 6OHDA. TH positive neurons number (labeled with a secondary antibody coupled to Alexa 488) was dramatically decreased by the application of 6OHDA. Igmesine protected neurons from cell death induced by 6OHDA treatment.
Conclusion Igmesine at 0.3 µM, 1 µM, and 3 µM shows a protective effect on dopaminergic neuron survival injured by 6OHDA (20 µM, 48 h). These results suggest that igmesine may have therapeutic interest in the treatment of Parkinson's disease.

Example 3

Effect of Igmesine on a Model of Huntington's Disease: Rat GABAergic Neuron Survival After Glutamate Injuries in Culture Rat Primary Cultures of Medium Spiny Neurons Rat MSN of striatum were cultured as described (Ivkovic S, et al, (1999) *The Journal of neuroscience: the official journal of the Society for Neuroscience* 19(13): 5409-5419).

Briefly pregnant female rats of 15 days gestation were killed by cervical dislocation (Rats Wistar; Janvier) and the foetuses removed from the uterus. The embryonic midbrains were removed and placed in ice-cold medium of Leibovitz 15 (L15; PanBiotech, Ref P04-27055, Batch: 8810315) containing 2% of Penicillin-Streptomycin (PS; PanBiotech, ref: P06-07100, Batch: 7511015) and 1% of bovine serum albumin (BSA; PanBiotech, Ref: P06-1391100, Batch: H140904). Only the ventral portions of the mesencephalic flexure were used for the cell preparations as this region of the developing brain is rich in dopaminergic neurons. The midbrains were dissociated by trypsinisation for 20 minutes (min) at 37° C. (Trypsin EDTA 1×; PanBiotech, Ref: P10-023100, batch: 1670415). The reaction was stopped by the addition of Dulbecco's modified Eagle's medium (DMEM; PanBiotech, Ref: P04-03600, Batch: 9021115) containing DNase I grade II (0.1 mg/ml; PanBiotech, Ref: P60-37780100, Batch: H140508) and 10% of fetal calf serum (FCS; Invitrogen, Ref: 10270-098, Batch: 41G8542K). Cells were then mechanically dissociated by 3 passages through a 10 ml pipet. Cells were then centrifuged at 180×g for 10 min at 4° C. on a layer of BSA (3.5%) in L15 medium. The supernatant was discarded and the cell pellets were re-suspended in a defined culture medium consisting of Neurobasal (Invitrogen, Ref: 21103, Batch: 1754639) supplemented with B27 (2%; Invitrogen, ref: 17504, batch: 1799273), L-glutamine (2 mM; PanBiotech, Ref: P04-80100, Batch: 6620314) and 2% of PS. Viable cells were counted in a Neubauer cytometer using the trypan blue exclusion test. The cells were seeded at a density of 70000 cells/well in 96 well-plates (pre-coated with poly-D-lysine; Greiner, Ref: E150033VJ) and were cultured at 37° C. in a humidified air (95%)/CO2 (5%) atmosphere. Half of the medium was changed every 2 days with fresh medium. In these conditions, after 5 days of culture, astrocytes are present in the culture and release growth factor allowing neurons differentiation. Five to six percent of the neuronal cell population was dopaminergic neurons.

Neuroprotective Effect of Igmesine (AMY002) on Rat MSNs

Briefly, after 11 days of culture, the medium was removed and fresh medium with test compound was added 2 hour before the intoxication. Then glutamate (40 µM, during 20 min) was added, with test compound. After 20 min of intoxication, the supernatant was changed with culture medium without glutamate and with igmesine during the next 24 hours after glutamate intoxication. The following conditions were done:
☐_Control medium during 20 min and during the next 24 hours
☐_Glutamate (40 µM), during 20 min and control medium during the next 24 hours.
☐_Glutamate (40 µM)+igmesine (0.1 µM, 0.3 µM, 1 µM, 3 µM, 10 µM, 30 µM, 100 µM) during 20 min and control medium+igmesine (0.1 µM, 0.3 µM, 1 µM, 3 µM, 10 µM, 30 µM, 100 µM) during the next 24 hours.

☐_Glutamate (40 µM)+BDNF (10 ng/ml) during 20 min and control medium+BDNF (10 ng/mL) during the next 24 hours.

One culture was done with 6 wells per condition.

End Point Evaluation: Measure of Total Number of DARPP32 Neurons

At the end of intoxication, cells were fixed by a solution of 4% paraformaldehyde (Sigma, ref 6148, batch: SLBH4356V) for 20 min at room temperature, the control conditions was fixed as well following the same procedure. The cells were then permeabilized and non-specific sites were blocked with a solution of phosphate buffered saline (PBS; PanBiotech; ref: P04-36500, Batch: 7250616) containing 0.1% of saponin (Sigma; ref: S7900, Batch: BCBJ8417V) and 1% fetal calf serum (FCS) for 15 min at room temperature. Cells were incubated with a rabbit polyclonal primary antibody anti-DARPP32 (Millipore) and with a mouse monoclonal primary antibody anti-MAP2 (Sigma) in PBS containing 1% FCS, 0.1% saponin, for 2 h at room temperature. These antibodies were revealed with Alexa Fluor 488 goat anti-mouse IgG (Molecular probe, ref: A11001, Batch: 011M4004V) and Alexa Fluor 568 goat anti-rabbit (Molecular probe, ref: A11011, Batch: 1670154) in PBS with 1% FCS, 0.1% saponin, for 1 h at room temperature. Nuclei of cells were labelled by a fluorescent marker (Hoechst solution, Sigma; ref: B1155, Batch: 011M4004V) in the same solution.

For each condition, 20 pictures per well were taken using InCell Analyzer™ 2000 (GE Healthcare) with 20× magnification. Images of each culture well were taken in same condition. Analysis of cell bodies of DARPP32 positive neurons was performed using Developer software (GE healthcare). A total of 6 data per experimental condition were provided.

Statistics

The data were expressed as mean±s.e.m. (of 6 data per condition, 1 culture). A global analysis of the data was performed using a one-way analysis of variance (ANOVA) following by Dunnett's test. The level of significance was set at $p<0.05$.

Results

Figure 19:
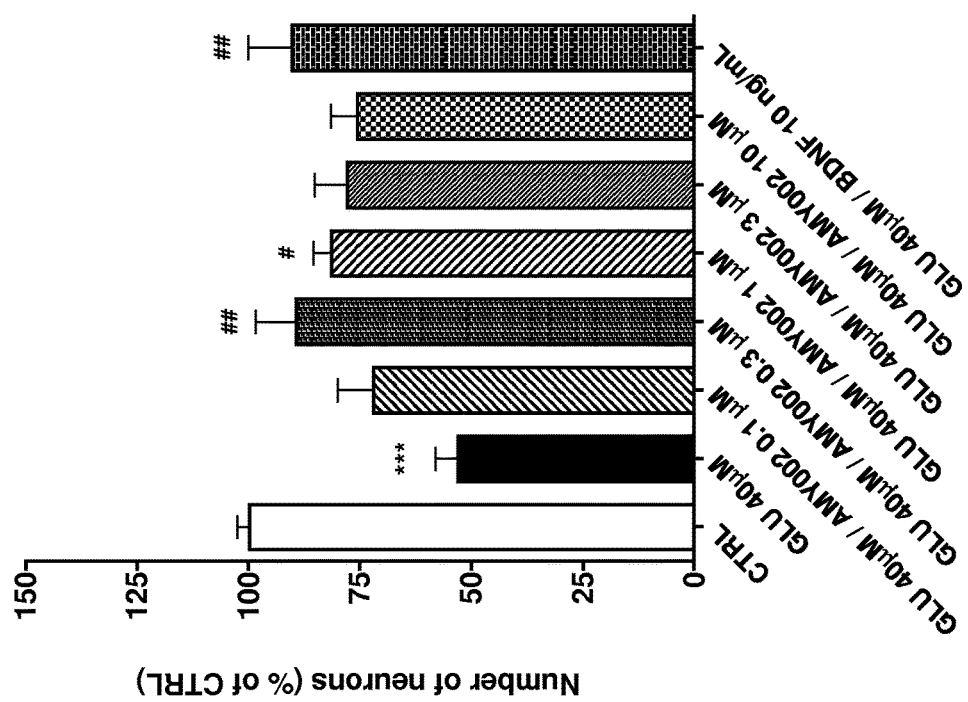
FIG. 19. Effect of igmesine (AMY002) on survival of primary medium spiny neurons (MSNs) injured by a high concentration of Glutamate (40 μM, 20 min) expressed in percentage of control (% of CTRL). The number of live neurons was expressed in percentage of untreated control (% of CTRL). The data were calculated as mean±s.e.m. using one way ANOVA followed by Dunnett's test. ***p<0.001 Glutamate vs control group. #p<0.05; ##p<0.01 igmesine or BDNF vs. Glutamate group. Glutamate induced a large and significant decrease of the number of DARPP32 positive neurons.

According to FIG. 19, Glutamate applied at 40 µM for 20 min induced a large and significant decrease of DARPP32 positive neurons (***$p<0.001$, 53.00% of the control). Application of BDNF (10 ng/mL) displays a protective effect against 6OHDA injury (##$p<0.01$, 90.14% of the control). This result validates the study. Igmesine (AMY002) at 0.3 µM and 1 µM shows a significant protective effect against glutamate (##$p<0.01$, 89.28% of the control and #$p<0.05$, 81.60% of the control). Glutamate induced a large and significant decrease of the number of DARPP32 positive neurons (MAP2 and DARPP32 labeled cells). Igmesine at 0.3 µM and 1 µM protected neurons from cell death induced by Glutamate.

Conclusion

Igmesine at 0.3 µM and 1 µM shows a protective effect on MSNs survival injured by Glutamate (40 µM, 20 min) indicating a potential interest of the compound for the treatment of Huntington's disease.

Example 4

Evaluation of the Neuroprotective Effect of Igmesine (AMY002) on Motor Neuron Survival After Glutamate Injury: a Model for Studying MND/ALS (Motor Neuron Diseases/Amyotrophic Lateral Sclerosis) Pathogenesis Motor Neuron Culture Rat motor neurons were cultured as described (Camu et al. (1994) *Journal of the neurological sciences* 124 Suppl: 73-74). Briefly, pregnant female rats of 14 days gestation were killed by cervical dislocation (Rats Wistar; Janvier Lab) and the foetuses were removed from the uterus. The spinal cord were removed and placed in ice-cold PBS. Tissue segments were spun down, incubated in 0.025% (w/v) of trypsin-EDTA (Panbiotech, Ref: P10-023100) for 10 min at 37° C. Fragments were transferred in 1 mL of complete Leibovitz medium containing BSA (0.4%, Dustcher, Ref: P06-1391100) and DNaseI grade II (0.1 mg/ml, Panbiotech, ref: P60-37780100). Cells were then dissociated by several rounds of trituration, centrifuged for 5 min at 470 g on a 4% BSA cushion and re-suspended in 2 mL of supplemented L15 medium. Motor neurons were counted in a Neubauer cytometer using the trypan blue exclusion test. Cells were cultured at a density of $1.5 \times 10^4$ cells/well of a 96 wells plate on astrocyte monolayer in Neurobasal (Invitrogen, ref: 21103) containing 1% of B27 (Invitrogen, ref: 17504), 2 mM L-Glutamine (Panbiotech, ref: P04-80100), 1% of PS solution, 25 mM 2-mercaptoethanol (Invitrogen, ref: 31350-010), 2% Horse serum (Invitrogen, Ref: 16050-122), 1 ng/ml of Brain-derived neurotrophic factor (BDNF, PanBiotech, Ref: CB-1115002) and 1 ng/ml of Glial derived neurotrophic factor (GDNF, Dustcher, Ref: CB-1116001) at 37° C. in a humidified air (95%)/$CO_2$ (5%) atmosphere.

Glutamate Intoxication and Drug Treatment

Briefly, after 10 days of culture, medium was removed and 100 µL of fresh medium (supplemented Neurobasal without neurotrophic factor) without or with test compound was added 1 h before glutamate intoxication. Then, Glutamate at 40 µM in absence or presence of test compound will be added in the culture medium and incubated 20 min. The cells were rinsed with incubation solution (3 wash-outs) and let in the neurobasal medium containing compounds or control medium for 24 h.

The followings were the experimental conditions:

☐_Control medium stimulated with vehicle medium
☐_Control medium stimulated with Glutamate (40 µM, 20 min)
☐_Igmesine (AMY002) at 7 concentrations (to be defined) stimulated with Glutamate (40 µM, 20 min)
☐_BDNF at 50 ng/mL stimulated with Glutamate (40 µM, 20 min)

End Point Evaluation: Measure of Total Number of Islet½ Positive Motor Neurons

At the end of intoxication, cells were fixed by a solution of 4% paraformaldehyde (Sigma, ref 6148, batch: SLBH4356V) for 20 min at room temperature, the control conditions was fixed as well following the same procedure. The cells were then permeabilized and non-specific sites were blocked with a solution of phosphate buffered saline (PBS; PanBiotech; ref: P04-36500, Batch: 1871016) containing 0.1% of saponin (Sigma; ref: S7900, Batch: BCBJ8417V), 4% goat serum (Gibco, Ref: 16210072, batch: 1517955) and 1% BSA (Dutsher, Ref: P06-1391100, batch: H140904) for 15 min at room temperature. Cells were incubated with a mouse primary antibody anti-Islet ½ (Hybridoma bank, Ref: 39.4D5-c, batch: 2/25/16-311 Ag/mL) and with a chicken primary antibody anti-MAP2 (Abcam, Ref: ab5392, batch: GR286806-3) in PBS containing 4% goat serum, 1% BSA, 0.1% saponin, overnight at room temperature. These antibodies were revealed with Alexa Fluor 488 goat anti-mouse IgG (Molecular probe, ref: A11001, Batch: 1752514) and Alexa Fluor 633 goat anti-chicken (Molecular probe, ref: A21449, Batch: 1698677) in PBS with 4% goat serum, 1% BSA, 0.1% saponin, for 1 h at room temperature. The nuclei of cells were labelled by a fluorescent marker (DAPI, Sigma; ref: B1155, Batch: 011M4004V) in the same solution.

For each condition, 20 pictures per well were taken using InCell Analyzer™ 2000 (GE Healthcare) with 20× magnification. Images of each culture well were taken in same condition. Analysis of cell bodies of Islet½ positive neurons was performed using Developer software (GE healthcare). A total of 6 data per experimental condition were provided.

Data Processing/Statistical Analysis

The data were expressed as mean±s.e.m (of 6 data per condition, 1 culture). A global analysis of the data was performed using a one-way analysis of variance (ANOVA) following by Dunnett's test. The level of statistical significance is set at $p<0.05$.

Results

Figure 20:
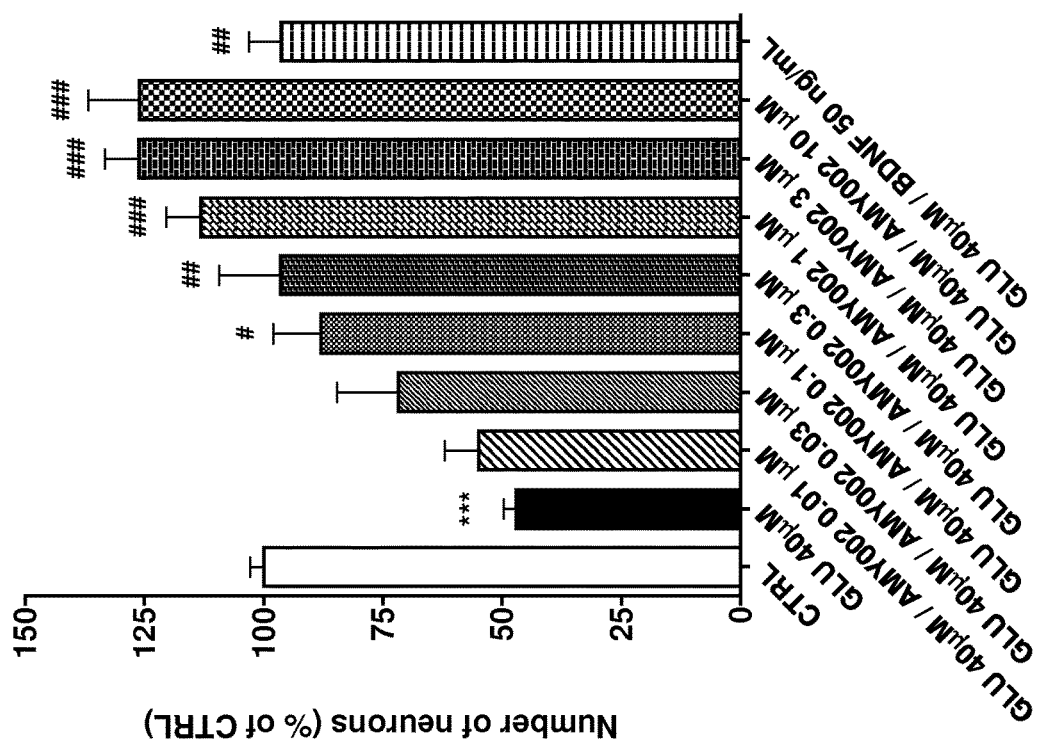
FIG. 20. Effect of igmesine (AMY002) on survival of primary motor neurons injured by Glutamate (40 μM, 20 min) expressed in percentage of control (% of CTRL). (mean±s.e.m; ***p<0.001 Glutamate vs control group; #p<0.05; ##p<0.01; ###p<0.001 igmesine or BDNF vs Glutamate group; one way ANOVA followed by Dunnett's test). Glutamate (40 μM, 20 min) induced a large and significant decrease of the number of ISLET ½ motor neurons.

According to FIG. 20, Glutamate applied at 40 µM for 20 min induced a large and significant decrease (***$p<0.001$, 47.17% of the control) of Islet ½ positive neurons labeled in red. Application of BDNF (50 ng/mL) displays a protective effect (##$p<0.01$, 96.43% of the control). This result validates the study.

Igmesine (AMY002) at 0.1 µM, 0.3 µM, 1 µM, 3 µM and 10 µM shows a significant protective effect against glutamate. Its action is the strongest at 10 µM (###$p<0.001$, 126% of the control). Interestingly, motor neuron survival was higher (but not significant) when the test compound was applied at 3 µM and 10 µM even in the presence of glutamate intoxication than in the control condition.

Conclusion:

Igmesine at 0.1 µM, 0.3 µM, 1 µM, and 3 µM and 10 µM shows a protective effect on motor neuron survival injured by Glutamate (40 µM, 20 min). These results strongly suggest the potential interest of the compound for the treatment of MND/ALS.

Example 5

Effect of Igmesine on Unfolded Protein Response (UPR)

The following demonstrates that igmesine promotes the dissociation of the sigma-1 receptor from another ER chaperone immunoglobulin heavy chain binding protein (BiP)/GRP78. When the sigma-1 receptor forms a complex with BiP, the chaperone activity is minimized. In contrast, the sigma-1 receptor dissociated from BiP exerts the maximum chaperone activity for misfolded proteins responsible for the UPR.

Material and Methods

CHO cells were grown in a 6-well plates and treated with the compounds in culture medium at 37° C. for 30 min at 1 µM and 10 µM final concentration. The reaction was stopped by medium removal and adding 3 mL PBS at 37° C. CHO cells were harvested and suspended in 50 mM HEPES (pH7.4) followed by cross-linking with 50 µg/ml of dithio (bis) succinimidyl propionate (Thermo Fisher Scientific, Waltham, Mass.) for 30 min at 4° C. The reaction was stopped by adding Tris-HCl (pH 8.8, final 50 mM). Fifteen minutes after incubation on ice, cells were lysed with RIPA buffer [50 mM Tris (pH7.4), 150 mM NaCl, 1% Triton X-100, 0.3% sodium deoxycholate, 0.1% SDS, protease inhibitor cocktail (Roche Complete)]. After centrifugation at 12,000 g, 1 min, the supernatant was incubated overnight at 4° C. with Sig-1R antibody (Abcam). The cell lysate was incubated with Sepharose protein-A (Invitrogen) for 90 min. After centrifugation at 12,000 g, 1 min, the supernatant was discarded and the pellet was washed in 0.5 mL RIPA buffer. After a second centrifugation at 12,000 g, 20 min, the supernatant was discarded and the pellet was washed in 0.5 mL 2× Sample buffer/bMCE buffer. Following a third centrifugation at 12,000 g, 1 min, the supernatant was analysed by ELISA assay, according to the manufacturer's protocol (USCNK #SEC343Mu).

Results and Discussion

Figure 21:
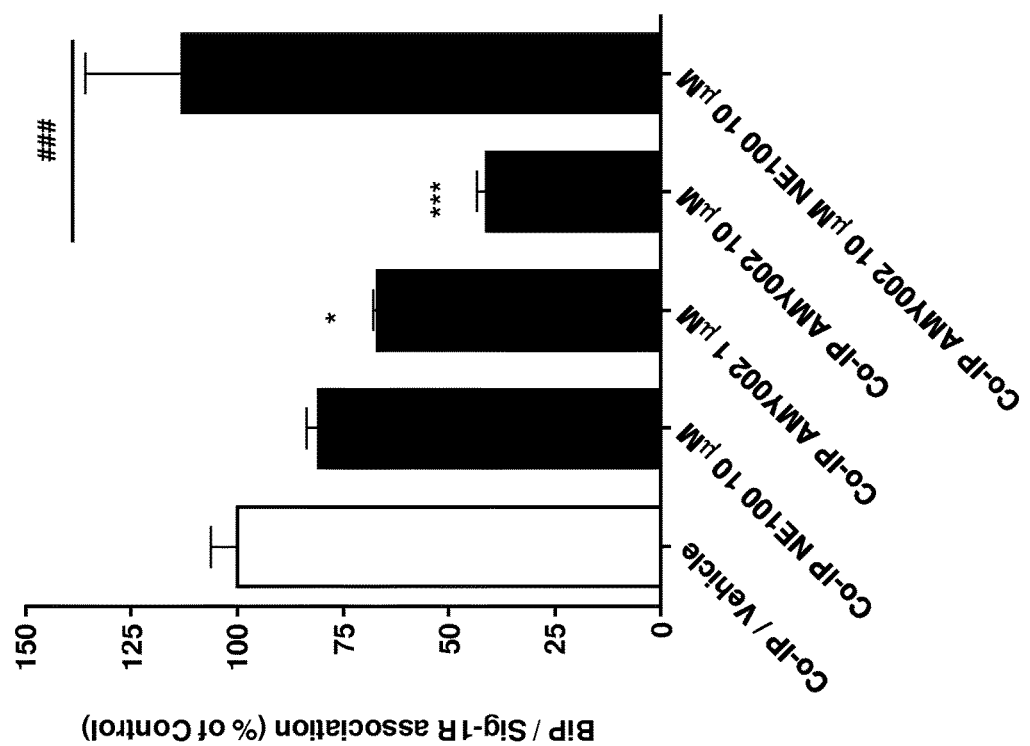
FIG. 21. Effect of igmesine (AMY002, 1 μM and 10 μM) on the dissociation of binding immunoglobulin protein (BiP) from sigma-1 receptor and antagonism of the dissociation effect by 10 μM NE100. * p<0.05, *** p<0.001 vs. the control group (Veh); ###p<0.001 vs. the 10 μM igmesine group; Dunnett's test.

As shown in FIG. 21, igmesine produced the dissociation of BiP from sigma-1 receptor in a dose-dependent manner. This dissociation was prevented by the sigma antagonist NE100.

These results demonstrate that igmesine is able to promote the dissociation of the sigma-1 receptor from BiP. This dissociation promotes the chaperone activity of sigma-1 receptors, thereby attenuating the accumulation of misfolded proteins in the cells. Such misfolded proteins, left to accumulate, would initiate the Unfolded Protein Response (UPR), which leads to activation of cell death pathways. Accordingly, the negative regulation of the UPR by the sigma-1 receptor limits cellular apoptosis induced by the accumulation of misfolded proteins. The agonist effect of igmesine on the chaperone activity of sigma-1 receptors makes igmesine a viable therapeutic candidate for neurodegenerative diseases and disorders such as Alzheimer's disease, amyotrophic lateral sclerosis, multiple sclerosis, Parkinson's disease, Huntington's disease, and frontotemporal degeneration. In addition, the same mechanism of action indicates that igmesine may also be active against transmissible prion encephalopathies such as Creutzfeldt-Jacod disease, these disorders differing in the proteins that misfold and the group of neurons which are affected.

What is claimed is:

1. A method for treating a neurodegenerative disease or disorder in a human subject in need thereof, the method-comprising administering to the subject a pharmaceutical composition comprising a therapeutically effective amount of igmesine, or a pharmaceutically acceptable salt thereof, wherein the igmesine is effective to delay or suppress the onset of one or more pathophysiological characteristics of the disease or disorder, or effective to delay or suppress the onset of at least one clinical symptom of the disease or disorder except depression, wherein the therapeutically effective amount of igmesine is in the range of from 1 to 20 mg per day.

2. The method-of claim 1, wherein the pharmaceutically acceptable salt is a hydrochloride salt.

3. The method of claim 1, wherein the composition is an oral dosage form adapted for once daily dosing.

4. The method of claim 1, wherein the neurodegenerative disease or disorder is selected from Alzheimer's disease, amyotrophic lateral sclerosis, multiple sclerosis, Parkinson's disease, Huntington's disease and frontotemporal dementia.

5. The method of claim 1, wherein the neurodegenerative disease or disorder is Alzheimer's disease or early onset Alzheimer's disease.

6. The method of claim 5, wherein the amount of igmesine is from 1 to 10 mg per day.

7. The method of claim 6, wherein the amount of igmesine is from 1 to 5 mg per day.

8. The method of claim 5, wherein the one or more pathophysiological characteristics of the Alzheimer's disease is selected from neuroinflammation, neuronal cell apoptosis, β amyloid plaque burden, tau protein hyperphosphorylation, and lipid peroxidation.

9. The method of claim 5, wherein the at least one clinical symptom of Alzheimer's disease is a learning or memory deficit associated with one or more of working memory, short term memory, long term memory, positively reinforced memory, spatial and contextual memory, or any combination of the foregoing.

10. A method for treating Alzheimer's disease or early onset Alzheimer's disease in a human subject in need thereof, the method comprising administering to the subject a pharmaceutical composition comprising a therapeutically effective amount of igmesine, or a pharmaceutically acceptable salt thereof, wherein the therapeutically effective amount of igmesine is in the range of from 1 to 20 mg per day, and wherein the igmesine is administered in combination with a cholinesterase inhibitor, a nonsteroidal anti-inflammatory agent, a monoamine oxidase B inhibitor, or a lipid lowering agent, and wherein the method is effective to delay or suppress the onset of at least one clinical symptom of Alzheimer's disease selected from a learning or memory deficit associated with one or more of working memory, short term memory, long term memory, positively reinforced memory, spatial and contextual memory, and combinations of the foregoing.

11. The method of claim 10, wherein the cholinesterase inhibitor is donepezil.

12. The method of claim 11, wherein the donepezil is present in an amount of from 1 to 15 mg.

13. The method of claim 10, wherein the igmesine is administered in combination with a nonsteroidal anti-inflammatory agent.

14. The method of claim 13, wherein the anti-inflammatory agent is ibuprofen.

15. The method of claim 14, wherein the ibuprofen is present in an amount of from 50 to 150 mg.

16. The method of claim 10, wherein the igmesine is administered in combination with a monoamine oxidase B inhibitor.

17. The method of claim 16, wherein the monoamine oxidase B inhibitor is selegiline.

18. The method of claim 17, wherein the selegiline is present in an amount of from 5 to 15 mg.

19. The method of claim 10, wherein the igmesine is administered in combination with a lipid lowering agent.

20. The method of claim 19, wherein the lipid lowering agent is atorvastatin.

21. The method of claim 20, wherein the atorvastatin is present in an amount of from 1 to 5 mg.

22. The method of claim 1, wherein the neurodegenerative disease or disorder is selected from Alzheimer's disease, Parkinson's disease, Amyotrophic Lateral Sclerosis, and Huntington's disease, the composition comprises igmesine hydrochloride in an amount of from 2.5 to 10 mg per dose, and the composition is adapted for administration one, two, or three times daily.

23. The method of claim 1, wherein the neurodegenerative disease or disorder is Amyotrophic Lateral Sclerosis (ALS).

24. The method of claim 10, wherein the amount of igmesine is from 1 to 10 mg per day.

25. The method of claim 10, wherein the amount of igmesine is from 1 to 5 mg per day.

* * * * *